United States Patent [19]
Albert et al.

[11] Patent Number: 5,919,653
[45] Date of Patent: Jul. 6, 1999

[54] NUCLEIC ACIDS ENCODING A HUMAN GLYCINE TRANSPORTER

[75] Inventors: Vivian R. Albert, Montclair; Leslie R. Z. Kowalski, Cedar Knolls; Laurence A. Borden, Hackensack, all of N.J.; Jeffrey F. McKelvy, New York, N.Y.

[73] Assignee: Allelix Neuroscience Inc., South Plainfield, N.J.

[21] Appl. No.: 08/700,013

[22] Filed: Aug. 20, 1996

[51] Int. Cl.[6] .................... C12N 15/12; C12N 15/85; C12N 15/63
[52] U.S. Cl. .............. 435/69.1; 435/320.1; 435/325; 536/23.5
[58] Field of Search ............... 536/23.5, 23.1, 536/24.3; 435/320.1, 325, 69.1; 935/9

[56] References Cited

U.S. PATENT DOCUMENTS

| | | | |
|---|---|---|---|
| 5,188,954 | 2/1993 | Lam et al. | 435/172.3 |
| 5,225,323 | 7/1993 | Lam et al. | 435/6 |
| 5,424,185 | 6/1995 | Lam et al. | 435/6 |

OTHER PUBLICATIONS

Blakely et al., Proc. Natl. Acad. Sci USA 85: 9846–9850, 1988.
Shimada et al., *Science*, 254: 576–578, 1991.
Johnson and Ascher, *Nature*, 325: 529–531, 1987.
Fletcher et al., *Glycine Neurotransmission*, Otterson and Storm–Mathisen, eds., 1990, pp. 193–219.
Smith et al., *Neuron*, 8: 927–935, 1992.
Liu et al., *J. Biol. Chem.*, 268:22802–22808, 1993.
Jursky and Nelson, *J. Neurochemistry*, 64:1026–1033, 1995.
Uhl, *Trends in Neuroscience*, 15:265–268, 1992.
Clark and Amara, *BioEssays*, 15:323–332, 1993.
Yaksh, *Pain*, 111–123, 1989.
Truong et al., *Movement Disorders*, 3:77–87, 1988.
Becker, *FASEB Journal*, 4:2767–2774, 1990.
Lopez–Corcuera et al., *J. Biol. Chem.*, 266:24809–24814, 1991.
Liu et al., *FEBS Letters*, 305:110–114, 1992.
Bannon et al., *J. Neurochem.*, 54:706–708, 1990.
Guastella et al., *Science*, 249:1303–1306, 1990.
Grimwood et al., *Molecular Pharmacology*, 49:923–930, 1992.
Kim et al., *Molecular Pharmacology*, 45:608–67, 1994.
Lu et al., *Proc. Nat'l. Acad. Sci. USA*, 88:6289–6292, 1991.
White et al., *J. Neurochemistry*, 35:503–512, 1989.
Becker et al., *J. Neuroscience*, 6:1358–1364, 1986.
Gibco. BRL Catalogue and Reference Guide (1992) p. 296.
Rudinger In "Peptide Hormones" (Jun. 1976) e.d. J. A. Parsons, University Park Press, Baltimore, pp. 1–7.

*Primary Examiner*—Paula K. Hutzell
*Assistant Examiner*—Robert C. Hayes
*Attorney, Agent, or Firm*—Dechert Price & Rhoads

[57] ABSTRACT

The invention provides nucleic acids and proteins derived from the sequence of the human GlyT-2 transporter of the amino acid glycine.

6 Claims, 11 Drawing Sheets

Alignment of human and rat GlyT-2 cDNA Sequences

Matcht 89.0

```
                 10         20         30         40         50         60
human    ATGGATTGCAGTGCTCCCAAGGAAATGAATAAACTGCCAGCCAACAGCCCGGAGGCGGCG
         ::::::::::::::::::::::::::::::::::   :::  ::::::: :   :::    :::
rat      ATGGATTGCAGTGCTCCCAAGGAAATGAATAAACCACCAACCAACATCTTGGA---GGCA
                210        220        230        240        250        260

70         80         90        100        110        120
human    GCGGCGCAGGGCCACCCGGATGGCCCATGCGCTCCCAGGACGAGCCCGGAGCAGGAGCTT
         :::  ::  ::::::::  ::::  ::::   :  :: ::  ::::: :::::: ::::::  :::
rat      ACGGTGCCGGGCCACCGGGATAGCCCTCGAGCACCTAGGACCAGCCCTGAGCAGGATCTT
                270        280        290        300        310        320

130        140        150        160        170
human    CCCGCGGCTGCCGCC-CCGCCGC--------CGCCACGTGTGCCCAGGTCCGCTTCCACC
         ::  :::::  :::  ::  :   ::::::               ::::::::::::::::::  ::::::::::
rat      CCTGCGGCAGCCCCCGCGGCCGCTGTCCAGCCGCCACGTGTGCCCAGGTCGGCTTCCACC
                330        340        350        360        370        380

180        190        200        210        220        230
human    GGCGCCCAAACTTTCCAGTCAGCGGACGCGCGAGCCTGCGAGGCTGAGCGGCCAGGAGTG
         :::::::::::::::::::::::  :::::  :::  ::::::  :::::  ::::::::  :::::
rat      GGCGCCCAAACTTTCCAGTCTGCGGATGCGAGAGCCTGTGAGGCACAGCGGCCTGGAGTA
                390        400        410        420        430        440

240        250        260        270        280        290
human    GGGTCTTGCAAACTCAGTAGCCCGCGGGCGCAGGCGGCCTCTGCAGCTCTGCGGGACTTG
         ::::  :::  :::::  ::  ::::::  :   :::  :: :::  :::::::::  ::  ::  ::::::::
rat      GGGTTTTGTAAACTTAGCAGCCCCCAGGCACAAGCGACCTCTGCGGCCCTCCGGGACTTA
                450        460        470        480        490        500

300        310        320        330        340        350
human    AGAGAGGCGCAAAGCGCGCAGGCCTCGCCCCCTCCCGGGAGCTCCGGGCCCGGCAACGCG
         ::  ::  :  :::  :::::  ::::::      ::::::  :::::   :  :  :::   :::::::::
rat      AGCGAAGGGCACAGCGCACAGGCCAATCCCCCTTCCGGGGCCGCTGGGGCTGGCAACGCT
                510        520        530        540        550        560

360        370        380        390        400        410
human    CTGCACTGTAAGATCCCTTCTCTGCGAGGCCCGGAGGGGGATGCGAACGTGAGTGTGGGC
         :  :::::  :::::  ::   :::::::  :::::::::::   :::  :  :::::::::::::::::  :
rat      TTACACTGCAAGATTCCAGCTCTGCGTGGCCCGGAGGAGGACGAGAACGTGAGTGTGGCC
                570        580        590        600        610        620

420        430        440        450        460        470
human    AAGGGCACCCTGGAGCGGAACAATACCCCTGTTGTGGGCTGGGTGAACATGAGCCAGAGC
         :::::::::  :::::::  :::::::::::::::   :::::::::::::::::  ::::::::::::::
rat      AAGGGCACGCTGGAGCACAACAATACCCCACCCGTGGGCTGGGTGAATATGAGCCAGAGC
                630        640        650        660        670        680
```

FIG. 3 A

```
               480        490        500        510        520        530
human   ACCGTGGTGCTGGGCACGGATGGAATCACGTCCGTGCTCCCGGGCAGCGTGGCCACCGTT
        ::  :::::  ::::  ::  ::::::::::::  ::::  :::::::::::::::::::::::::  :
rat     ACAGTGGTGTTGGGTACCGATGGAATCGCGTCGGTGCTCCCGGGCAGCGTGGCCACCACT
               690        700        710        720        730        740

540        550        560        570        580        590
human   GCCACCCAGGAGGACGAGCAAGGGGATGAGAATAAGGCCCGAGGGAACTGGTCCAGCAAA
        :::  :  :::::::::::::::::::::::::::::::::  :::::::::::::::::::::
rat     ACCATTCCGGAGGACGAGCAAGGGGATGAGAATAAGGCCAGAGGGAACTGGTCCAGCAAA
               750        760        770        780        790        800

600        610        620        630        640        650
human   CTGGACTTCATCCTGTCCATGGTGGGGTACGCAGTGGGGCTGGGCAATGTCTGGAGGTTT
        :::::::::::::::::::::::::::::::::::::::::::::  :::::  ::::::::::
rat     CTGGACTTCATCCTGTCCATGGTGGGGTACGCAGTGGGGCTGGGTAATGTTTGGAGGTTT
               810        820        830        840        850        860

660        670        680        690        700        710
human   CCCTACCTGGCCTTCCAGAACGGGGGAGGTGCTTTCCTCATCCCTTACCTGATGATGCTG
        ::::::::::::::::::::::::::::::::::::::::::::::::::::::  ::::::::::::
rat     CCCTACCTGGCCTTCCAGAACGGGGGAGGTGCTTTCCTCATCCCTTACTTGATGATGCTG
               870        880        890        900        910        920

720        730        740        750        760        770
human   GCTCTGGCTGGATTACCCATCTTCTTCTTGGAGGTGTCGCTGGGCCAGTTTGCCAGCCAG
        ::  :::::::::  :::::  ::::::::::::  :  :::::::::  ::::::::::::::::::::::
rat     GCACTGGCTGGCTTACCTATCTTCTTCCTAGAGGTGTCCCTGGGCCAGTTTGCCAGCCAG
               930        940        950        960        970        980

780        790        800        810        820        830
human   GGACCAGTGTCTGTGTGGAAGGCCATCCCAGCTCTACAAGGCTGTGGCATCGCGATGCTG
        ::  ::  :::::::::::::::::::::::::::::::  ::  :::::::::::  :::::::::
rat     GGTCCTGTGTCTGTGTGGAAGGCCATCCCAGCTCTGCAGGGCTGTGGCATTGCGATGCTC
               990        1000       1010       1020       1030       1040

840        850        860        870        880        890
human   ATCATCTCTGTCCTAATAGCCATATACTACAATGTGATTATTTGCTATACACTTTTCTAC
        :::::::  :::::  :::::::::  ::::::::::  ::  ::  :::::  ::  ::  :::::::
rat     ATCATCTCCGTCCTCATAGCCATCTACTACAACGTCATCATCTGCTACACGCTCTTCTAC
               1050       1060       1070       1080       1090       1100

900        910        920        930        940        950
human   CTGTTTGCCTCCTTTGTGTCTGTACTACCCTGGGGCTCCTGCAACAACCCTTGGAATACG
        ::::::::  ::  :::::::::::::  ::  :::::::::  :::::::::::::  ::::  ::
rat     CTGTTTGCTTCTTTTGTGTCTGTGCTGCCCTGGGGATCCTGCAACAACCCGTGGAACACA
               1110       1120       1130       1140       1150       1160

960        970        980        990        1000       1010
human   CCAGAATGCAAAGATAAAACCAAACTTTTATTAGATTCCTGTGTTATCAGTGACCATCCC
        :::::::::::::::::::::  :::::::::::::::/  ::::::::::::::::  :::::::::::
rat     CCAGAATGCAAAGACAAAACCAAACTTTTACTAGATTCCTGTGTTATCGGTGACCATCCC
               1170       1180       1190       1200       1210       1220
```

FIG. 3B

```
              1020       1030       1040       1050       1060       1070
human   AAAATACAGATCAAGAACTCGACTTTCTGCATGACCGCTTATCCCAACGTGACAATGGTT
        ::  ::::::::::::::::::: :::::::::::: ::  :::::  ::: :::::: ::::::
rat     AAGATACAGATCAAGAACTCTACTTTCTGCATGACTGCCTATCCGAACTTGACCATGGTT
              1230       1240       1250       1260       1270       1280

1080       1090       1100       1110       1120       1130
human   AATTTCACCAGCCAGGCCAATAAGACATTTGTCAGTGGAAGTGAAGAGTACTTCAAGTAC
        ::  :::::::::::::::::::::::::::::::: ::  :::::::::::::::::::::
rat     AACTTCACCAGCCAGGCCAATAAGACATTTGTCAGCGGGAGTGAAGAGTACTTCAAGTAC
              1290       1300       1310       1320       1330       1340

1140       1150       1160       1170       1180       1190
human   TTTGTGCTGAAGATTTCTGCAGGGATTGAATATCCTGGCGAGATCAGGTGGCCACTAGCT
        ::::::::::::::::::::::::::::::::::::::::  ::::::::::::::  :  :
rat     TTTGTGCTGAAGATTTCTGCAGGGATTGAATATCCTGGTGAGATCAGGTGGCCCTTGCCG
              1350       1360       1370       1380       1390       1400

1200       1210       1220       1230       1240       1250
human   CTCTGCCTCTTCCTGGCTTGGGTCATTGTGTATGCATCGTTGGCTAAAGGAATCAAGACT
        :::::::  :::::::::  :::::  :::::  :::::::::  :::: :::::::  :::::
rat     TTCTGCCTTTTCCTGGCCTGGGTGATTGTATATGCATCGCTGGCAAAAGGAATTAAGACA
              1410       1420       1430       1440       1450       1460

1260       1270       1280       1290       1300       1310
human   TCAGGAAAAGTGGTGTACTTCACGGCCACGTTCCCGTATGTCGTACTCGTGATCCTCCTC
        ::::::::::::::::::::::::::  ::::: :::::  :::::::::  ::  :: ::::::::
rat     TCAGGAAAAGTGGTGTACTTCACAGCCACCTTCCCCTTATGTCGTCCTGGTCATCCTCCTC
              1470       1480       1490       1500       1510       1520

1320       1330       1340       1350       1360       1370
human   ATCCGAGGAGTCACCCTGCCTGGAGCTGGAGCTGGGATCTGGTACTTCATCACACCCAAG
        ::  :::::  ::::::::::::::::::::::::  :: ::::::::::::::::::::: :::
rat     ATTCGAGGGGTCACCCTGCCTGGAGCTGGAGCCGGTATCTGGTACTTCATCACACCTAAG
              1530       1540       1550       1560       1570       1580

1380       1390       1400       1410       1420       1430
human   TGGGAGAAACTCACGGATGCCACGGTGTGGAAAGATGCTGCCACTCAGATTTTCTTCTCT
        :::::::::::::::::::::::::::::::::::  :::::  :::::::::::::::::::
rat     TGGGAGAAACTCACGGATGCCACGGTGTGGAAGGATGCAGCCACTCAGATTTTCTTCTCC
              1590       1600       1610       1620       1630       1640

1440       1450       1460       1470       1480       1490
human   TTATCTGCTGCATGGGGAGGCCTGATCACTCTCTCTTCTTACAACAAATTCCACAACAAC
        :  :::::  ::  ::::::::::  ::  ::::::::: :::::::::::::::: ::::::
rat     CTGTCTGCGGCCTGGGGAGGGCTCATCACTCTTTCTTCTTACAACAAATTCCATAACAAC
              1650       1660       1670       1680       1690       1700

1500       1510       1520       1530       1540       1550
human   TGCTACAGGGACACTCTAATTGTCACCTGCACCAACAGTGCCACAAGCATCTTTGCCGGC
        ::::::::::::::::  :::::::::  ::::::::::::::::::::::::::  ::  ::
rat     TGCTACAGGGACACGTTAATTGTAACCTGCACCAACAGTGCCACTAGCATCTTCGCTGGG
              1710       1720       1730       1740       1750       1760
```

FIG. 3 C

```
              1560       1570       1580       1590       1600       1610
human   TTCGTCATCTTCTCCGTTATCGGCTTCATGGCCAATGAACGCAAAGTCAACATTGAGAAT
        ::  :::::::::::: ::  :  :::::::::: ::  :::::::::::::::::::::
rat     TTTGTCATCTTCTCTGTCATTGGCTTCATGGCCAACGAGCGCAAAGTCAACATTGAGAAT
              1770       1780       1790       1800       1810       1820

1620       1630       1640       1650       1660       1670
human   GTGGCAGACCAAGGGCCAGGCATTGCATTTGTGGTTTACCCGGAAGCCTTAACCAGGCTG
        ::::: ::::::::::::::::::::::::::::::::::::: ::::::::::::::::
rat     GTGGCTGACCAAGGGCCAGGCATTGCATTTGTGGTTTACCCAGAAGCCTTAACCAGGCTG
              1830       1840       1850       1860       1870       1880

1680       1690       1700       1710       1720       1730
human   CCTCTCTCCGTTCTGGGCCATCATCTTTTTCCTGATGCTCCTCACTCTTGGACTTGAC
        :::::::::: :::::::::::::::::::::::::::: :::::  :::::::::::::
rat     CCTCTCTCCATTCTGGGCCATCATCTTTTTCCTGATGCTTCTCACGCTTGGACTTGAC
              1890       1900       1910       1920       1930       1940

1740       1750       1760       1770       1780       1790
human   ACTATGTTTGCCACCATCGAGACCATAGTGACCTCCATCTCAGACGAGTTTCCCAAGTAC
        ::  :::::::: :::::::::::::: ::::::::::::: :: :::::::::::::::
rat     ACCATGTTTGCTACCATCGAGACCATTGTGACCTCCATCTCGGATGAGTTTCCCAAGTAT
              1950       1960       1970       1980       1990       2000

1800       1810       1820       1830       1840       1850
human   CTACGCACACACAAGCCAGTGTTTACTCTGGGCTGCTGCATTTGTTTCTTCATCATGGGT
        ::  ::::::::::::::: :::::  :::::::::::::::  :: ::::  : ::::
rat     CTGCGCACACACAAGCCTGTGTTCACCCTGGGCTGCTGCATCTGCTTCTTCATTATGGGC
              2010       2020       2030       2040       2050       2060

1860       1870       1880       1890       1900       1910
human   TTTCCAATGATCACTCAGGGTGGAATTTACATGTTTCAGCTTGTGGACACCTATGCTGCC
        :: :::::::::::: ::::::::::: :::::::::::::::::::::::::::::::
rat     TTCCCAATGATCACACAGGGTGGAATCTACATGTTTCAGCTTGTGGACACCTATGCTGCC
              2070       2080       2090       2100       2110       2120

1920       1930       1940       1950       1960       1970
human   TCCTATGCCCTTGTCATCATTGCCATTTTTGAGCTCGTGGGGATCTCTTATGTGTATGGC
        :::::::: :::::::::::::::::: :::::::: :: :: ::::: :::::: :::
rat     TCCTATGCTCTTGTCATCATTGCCATATTTGAGCTTGTTGGCATCTCCTATGTGTACGGC
              2130       2140       2150       2160       2170       2180

1980       1990       2000       2010       2020       2030
human   TTGCAAAGATTCTGTGAAGATATAGAGATGATGATTGGATTCCAGCCTAACATCTTCTGG
        :::::  :: :::::::::: :: :::::::::::::::::::::::: :::: ::::::
rat     TTGCAGAGGTTCTGTGAAGACATCGAGATGATGATTGGATTCCAGCCCAACATTTTCTGG
              2190       2200       2210       2220       2230       2240

2040       2050       2060       2070       2080       2090
human   AAAGTCTGCTGGGCATTTGTAACCCCAACCATTTTAACCTTTATCCTTTGCTTCAGCTTT
        :: ::::::::::: :::::::  :: ::::::::::: :::::::::::::::::::
rat     AAGGTCTGCTGGGCGTTTGTCACACCGACCATTTTAACGTTTATCCTTTGCTTCAGCTTC
              2250       2260       2270       2280       2290       2300
```

FIG. 3D

```
              2100       2110       2120       2130       2140       2150
human    TACCAGTGGGAGCCCATGACCTATGGCTCTTACCGCTATCCTAACTGGTCCATGGTGCTC
         :: :::::::::::::::::::::::::::: :::::::: :::::::::::::::::::
rat      TATCAGTGGGAGCCCATGACCTATGGCTCCTACCGCTACCCTAACTGGTCCATGGTGCTT
              2310       2320       2330       2340       2350       2360

2160       2170       2180       2190       2200       2210
human    GGATGGCTAATGCTCGCCTGTTCCGTCATCTGGATCCCAATTATGTTTGTGATAAAAATG
         :::::::: ::::::::::: :::: ::::::::::: :::::::: ::::::::::::
rat      GGATGGCTGATGCTCGCCTGCTCCGTGATCTGGATCCCGATTATGTTCGTGATAAAAATG
              2370       2380       2390       2400       2410       2420

2220       2230       2240       2250       2260       2270
human    CATCTGGCCCCTGGAAGATTTATTGAGAGGCTGAAGTTGGTGTGCTCGCCACAGCCGGAC
         :::::: ::::: :::::::::::::::::::::::::: :::::::::::::::::::
rat      TATCTGGCTCCTGGGAGATTTATTGAGAGGCTGAAGTTGGTATGCTCGCCACAGCCGGAC
              2430       2440       2450       2460       2470       2480

2280       2290       2300       2310       2320       2330
human    TGGGGCCCATTCTTAGCTCAACACCGCGGGGAGCGTTACAAGAACATGATCGACCCCTTG
         :::::::::::::::::::::: ::::::::::: :: :::::::: :::::::::::::
rat      TGGGGCCCATTCTTAGCTCAGCACCGCGGGGAACGCTACAAGAATATGATCGACCCCTTG
              2490       2500       2510       2520       2530       2540

2340       2350       2360       2370       2380       2390
human    GGAACCTCTTCCTTGGGACTCAAACTGCCAGTGAAGGATTTGGAACTGGGCACTCAGTGC
         ::::::: ::: :::::::::::: :::::::::::::::::::::::::::: :::::
rat      GGAACCTCGTCCCTGGGACTCAAGCTGCCAGTGAAGGATTTGGAACTGGGCACCCAGTGC
              2550       2560       2570       2580       2590       2600 human    TAGTCC
         ::::::
rat      TAGTCC
              2610
```

FIG. 3 E

Alignment of human and rat GlyT-2 amino acid sequences

```
Match: 94.4

10          20          30          40          50
human    MDCSAPKEMNKLPANSPEAAAAQGHPDGPCAPRTSPEQELPAAA---APPPPRVPRSAST
         ::::::::::: :.: ::... ::.:: ::::::::.::::: : .:::::::::::
rat      MDCSAPKEMNKPPTNILEATVP-GHRDSPRAPRTSPEQDLPAAAPAAAVQPPRVPRSAST
                10          20         30          40          50

60          70          80          90         100         110
human    GAQTFQSADARACEAERPGVGSCKLSSPRAQAASAALRDLREAQSAQASPPPGSSGPGNA
         :::::::::::::::.:::::  ::::::.::: ::::::::::.:...:::.::.:.:::
rat      GAQTFQSADARACEAQRPGVGFCKLSSPQAQATSAALRDLSEGHSAQANPPSGAAGAGNA
                60          70          80          90         100         110

120         130         140         150         160         170
human    LHCKIPSLRGPEGDANVSVGKGTLERNNTPVVGWVNMSQSTVVLGTDGITSVLPGSVATV
         ::::::.,::::::.:.::::.::::: :::::::::::::::::::::::.:::::::.
rat      LHCKIPALRGPEEDENVSVAKGTLEHNNTPPVGWVNMSQSTVVLGTDGIASVLPGSVATT
               120         130         140         150         160         170

180         190         200         210         220         230
human    ATQEDEQGDENKARGNWSSKLDFILSMVGYAVGLGNVWRFPYLAFQNGGGAFLIPYLMML
         ...:::::::::::::::::::::::::::::::::::::::::::::::::::::::
rat      TIPEDEQGDENKARGNWSSKLDFILSMVGYAVGLGNVWRFPYLAFQNGGGAFLIPYLMML
               180         190         200         210         220         230

240         250         260         270         280         290
human    ALAGLPIFFLEVSLGQFASQGPVSVWKAIPALQGCGIAMLIISVLIAIYYNVIICYTLFY
         ::::::::::::::.:::::::::::::::::::::::.::::::::::::::::::::
rat      ALAGLPIFFLEVSLGQFASQGPVSVWKAIPALQGCGIAMLIISVLIAIYYNVIICYTLFY
               240         250         260         270         280         290

300         310         320         330         340         350
human    LFASFVSVLPWGSCNNPWNTPECKDKTKLLLDSCVISDHPKIQIKNSTFCMTAYPNVTMV
         ::::::::::::::::::::::::::::::::::::.:::::::::::::::::.:::
rat      LFASFVSVLPWGSCNNPWNTPECKDKTKLLLDSCVIGDHPKIQIKNSTFCMTAYPNLTMV
               300         310         320         330         340         350

360         370         380         390         400         410
human    NFTSQANKTFVSGSEEYFKYFVLKISAGIEYPGEIRWPLALCLFLAWVIVYASLAKGIKT
         :::::::::::::::::::::::::::::::::::::::..::::::::::::::::::
rat      NFTSQANKTFVSGSEEYFKYFVLKISAGIEYPGEIRWPLPFCLFLAWVIVYASLAKGIKT
               360         370         380         390         400         410

420         430         440         450         460         470
human    SGKVVYFTATFPYVVLVILLIRGVTLPGAGAGIWYFITPKWEKLTDATVWKDAATQIFFS
         ::::::::::::::::::::::::::::::::::::::::::::::::::::::::::
rat      SGKVVYFTATFPYVVLVILLIRGVTLPGAGAGIWYFITPKWEKLTDATVWKDAATQIFFS
               420         430         440         450         460         470
```

FIG. 4A

```
               480        490        500        510        520        530
human     LSAAWGGLITLSSYNKFHNNCYRDTLIVTCTNSATSIFAGFVIFSVIGFMANERKVNIEN
          ::::::::::::::::::::::::::::::::::::::::::::::::::::::::::::
rat       LSAAWGGLITLSSYNKFHNNCYRDTLIVTCTNSATSIFAGFVIFSVIGFMANERKVNIEN
               480        490        500        510        520        530

540        550        560        570        580        590
human     VADQGPGIAFVVYPEALTRLPLSPFWAIIFFLMLLTLGLDTMFATIETIVTSISDEFPKY
          ::::::::::::::::::::::::::::::::::::::::::::::::::::::::::::
rat       VADQGPGIAFVVYPEALTRLPLSPFWAIIFFLMLLTLGLDTMFATIETIVTSISDEFPKY
               540        550        560        570        580        590

600        610        620        630        640        650
human     LRTHKPVFTLGCCICFFIMGFPMITQGGIYMFQLVDTYAASYALVIIAIFELVGISYVYG
          ::::::::::::::::::::::::::::::::::::::::::::::::::::::::::::
rat       LRTHKPVFTLGCCICFFIMGFPMITQGGIYMFQLVDTYAASYALVIIAIFELVGISYVYG
               600        610        620        630        640        650

660        670        680        690        700        710
human     LQRFCEDIEMMIGFQPNIFWKVCWAFVTPTILTFILCFSFYQWEPMTYGSYRYPNWSMVL
          ::::::::::::::::::::::::::::::::::::::::::::::::::::::::::::
rat       LQRFCEDIEMMIGFQPNIFWKVCWAFVTPTILTFILCFSFYQWEPMTYGSYRYPNWSMVL
               660        670        680        690        700        710

720        730        740        750        760        770
human     GWLMLACSVIWIPIMFVIKMHLAPGRFIERLKLVCSPQPDWGPFLAQHRGERYKNMIDPL
          :::::::::::::::::::::::::.::::::::::::::::::::::::::::::::::
rat       GWLMLACSVIWIPIMFVIKMYLAPGRFIERLKLVCSPQPDWGPFLAQHRGERYKNMIDPL
               720        730        740        750        760        770

780        790
human     GTSSLGLKLPVKDLELGTQC
          ::::::::::::::::::::
rat       GTSSLGLKLPVKDLELGTQC
               780        790
```

FIG. 4B

NUCLEIC ACIDS ENCODING A HUMAN GLYCINE TRANSPORTER

This application is related to the following co-pending applications: "Glycine Transporter-Transfected Cells and Uses Thereof," Ser. No. 08/655,836, filed May 31, 1996; "Pharmaceutical For Treatment Of Neurological And Neuropsychiatric Disorders," Ser. No. 08/656,063, filed May 31, 1996, now a provisional application "Pharmaceutical For Treatment of Neuropsychiatric Disorders," Ser. No. 08/655,912, filed May 31, 1996, now a provisional application and "Pharmaceutical For Treating Of Neurological and Neuropsychiatric Disorders," Ser. No. 08/655,847, filed May 31, 1996, now a provisional application The present invention relates to nucleic acid encoding the "GlyT-2" member of the family of human glycine transporters, to the isolated protein encoded by the nucleic acid, and to the field of drug discovery.

Synaptic transmission is a complex form of intercellular communication that involves a considerable array of specialized structures in both the pre- and post-synaptic neuron. High-affinity neurotransmitter transporters are one such component, located on the pre-synaptic terminal and surrounding glial cells (Kanner and Schuldiner, *CRC Critical Reviews in Biochemistry* 22: 1032, 1987). Transporters sequester neurotransmitter from the synapse, thereby regulating the concentration of neurotransmitter in the synapse, as well as its duration in the synapse, which together influence the magnitude of synaptic transmission. By preventing the spread of transmitter to neighboring synapses, transporters maintain the fidelity of synaptic transmission. Further, by sequestering released transmitter into the presynaptic terminal, transporters allow for transmitter reutilization.

Neurotransmitter transport is dependent on extracellular sodium and the voltage difference across the membrane; under conditions of intense neuronal firing, as for example during a seizure, transporters can function in reverse, releasing neurotransmitter in a calcium-independent non-exocytotic manner (Attwell et al., *Neuron* 11: 401–407, 1993). Pharmacologic modulation of neurotransmitter transporters thus provides a means for modifying synaptic activity, which provides useful therapy for the treatment of neurological and psychiatric disturbances.

The amino acid glycine is a major neurotransmitter in the mammalian nervous system, functioning at both inhibitory and excitatory synapses. By nervous system, both the central and peripheral portions of the nervous system are intended. The distinct inhibitory and excitatory functions of glycine are mediated by two different types of receptor, each of which is associated with a different class of glycine transporter. The inhibitory actions of glycine are mediated by glycine receptors that are sensitive to the convulsant alkaloid, strychnine, and are thus referred to as "strychnine-sensitive". Such receptors contain an intrinsic chloride channel that is opened upon binding of glycine to the receptor; by increasing chloride conductance, the threshold for firing of an action potential is increased. Strychnine-sensitive glycine receptors are found predominantly in the spinal cord and brainstem, and pharmacological agents that enhance the activation of such receptors will thus increase inhibitory neurotransmission in these regions.

Glycine functions in excitatory transmission by modulating the actions of glutamate, the major excitatory neurotransmitter in the central nervous system. See Johnson and Ascher, *Nature* 325: 529–531, 1987; Fletcher et al., *Glycine Transmission* Otterson and Storm-Mathisen, eds., 1990, pp. 193–219. Specifically, glycine is an obligatory co-agonist at the class of glutamate receptor termed N-methyl-D-aspartate (NMDA) receptor. Activation of NMDA receptors on a neuron increases sodium and calcium conductance, which depolarizes the neuron, thereby increasing the likelihood that the neuron will fire an action potential. NMDA receptors are widely distributed throughout the brain, with a particularly high density in the cerebral cortex and hippocampal formation.

Molecular cloning has revealed the existence in mammalian brains of two classes of glycine transporters, termed GlyT-1 and GlyT-2. GlyT-1 is found predominantly in the forebrain, and its distribution corresponds to that of glutamatergic pathways and NMDA receptors (Smith, et al., *Neuron* 8: 927–935, 1992). The distribution of GlyT-2 differs; this transporter is found predominantly in the brain stem and spinal cord, and its distribution corresponds closely to that of strychnine-sensitive glycine receptors. Liu et al., *J. Biol. Chem.* 268: 22802–22808, 1993; Jursky and Nelson, *J. Neurochem.* 64: 1026–1033, 1995. These observations are consistent with the view that, by regulating the synaptic levels of glycine, GlyT-1 and GlyT-2 preferentially influence the activity of NMDA receptors and strychnine-sensitive glycine receptors, respectively.

Sequence comparisons of GlyT-1 and GlyT-2 have revealed that these glycine transporters are members of a broader family of sodium-dependent neurotransmitter transporters, including, for example, transporters specific for γ-amino-n-butyric acid (GABA) and others. Uhl, *Trends in Neuroscience* 15: 265–268, 1992; Clark and Amara, *BioEssays* 15: 323–332, 1993. Overall, each of these transporters includes 12 putative transmembrane domains that predominantly contain hydrophobic amino acids. Comparing rat GlyT-1 to rat GlyT-2, using the Lipman-Pearson FASTA algorithm, reveals a 51% amino acid sequence identity and a 55% nucleic acid sequence identity. Comparison of the sequence of human GlyT-1 with rat GlyT-2 reveals a 51% amino acid sequence identity and a 53–55% nucleic acid sequence identity, with the range of values for nucleic acid sequence identity resulting from the existence of three variant forms of GlyT-1.

Compounds that inhibit or activate glycine transporters would be expected to alter receptor function, and provide therapeutic benefits in a variety of disease states. For example, inhibition of GlyT-2 can be used to diminish the activity of neurons having strychnine-sensitive glycine receptors via increasing synaptic levels of glycine, thus diminishing the transmission of pain-related (i.e., nociceptive) information in the spinal cord, which has been shown to be mediated by these receptors. Yaksh, *Pain* 111–123, 1989. Additionally, enhancing inhibitory glycinergic transmission through strychnine-sensitive glycine receptors in the spinal cord can be used to decrease muscle hyperactivity, which is useful in treating diseases or conditions associated with increased muscle contraction, such as spasticity, myoclonus (which relates to rapid muscle spasms), and epilepsy (Truong et al., *Movement Disorders* 3: 77–87, 1988; Becker, *FASEB J.* 4: 2767–2774, 1990). Spasticity that can be treated via modulation of glycine receptors is associated with epilepsy, stroke, head trauma, multiple sclerosis, spinal cord injury, dystonia, and other conditions of illness and injury of the nervous system.

SUMMARY OF THE INVENTION

In a first embodiment, the invention provides a nucleic acid encoding a glycine transporter having at least about 96% sequence identity with the protein sequence of SEQ ID 19 or with a sequence corresponding to the protein sequence of SEQ ID 19 except that it has one or more of the following substitutions (1) $Ser^{102}$ to Gly, (2) $Ser^{124}$ to Phe, (3) $Ile^{279}$ to Asn, (4) $Arg^{393}$ to Gly, (5) $Lys^{457}$ to Asn, (6) $Asp^{463}$ to Asn, (7) $Cys^{610}$ to Tyr, (8) $Ile^{611}$ to Val, (9) $Phe^{733}$ to Ser or (10) $Ile^{735}$ to Val. Preferably, the sequence identity is at least about 97%, more preferably at least about 98%, yet more preferably at least about 99%, yet more preferably at least about 99.5%. In an embodiment of the invention, the sequence identity is 100%. Preferably, the encoded glycine transporter has no more than four amino acid differences in the region from amino acid 200 to 797 of the protein sequence of SEQ ID 19 or of a sequence corresponding to the protein sequence of SEQ ID 19 except that it has one of the substitutions described above, more preferably no more than two such differences.

The invention also provides a vector comprising the nucleic acid described above. In one embodiment, the vector is effective to express a glycine transporter mRNA in at least one of a bacterial cell or a eukaryotic cell. In another embodiment of the invention, the vector is effective to express the mRNA in at least one of a yeast cell, a mammalian cell or an avian cell.

The invention further provides an isolated glycine transporter derived from transformed cells according to the invention, the transporter comprising the amino acid sequence encoded by the above-described nucleic acid or one to two contiguous portions of amino acid sequence encoded by such a nucleic acid, wherein the protein has glycine transporter activity and differs in sequence from the aligned segments of the rat transporter sequence. The phrase "contiguous sequence," as used herein, refers to uninterupted portions of the relevant reference nucleic acid or amino acid sequence. Preferably, the glycine transporter protein of the present invention differs in sequence from the aligned segments of the rat transporter sequence by at least two amino acids, more preferably, at least four amino acids. Preferably, the contiguous sequences comprise at least about 600 amino acids, more preferably at least about 700 amino acids, more preferably at least about 750 amino acids. In one embodiment, the transporter protein comprises all of the protein sequence encoded by the above-described nucleic acid. Preferably, the transporter protein comprises amino acid sequence set forth in the protein sequence of SEQ ID 19 or a sequence corresponding to the protein sequence of SEQ ID 19 except that it has one or more of the following substitutions (1) $Ser^{102}$ to Gly, (2) $Ser^{124}$ to Phe, (3) $Ile^{279}$ to Asn, (4) $Arg^{393}$ to Gly, (5) $Lys^{457}$ to Asn, (6) $Asp^{463}$ to Asn, (7) $Cys^{610}$ to Tyr, (8) $Ile^{611}$ to Val, (9) $Phe^{733}$ to Ser or (10) $Ile^{735}$ to Val, or an amino acid sequence comprising one to two contiguous portions of these sequences. In a preferred embodiment, the invention provides a glycine transporter and associated nucleic acids, vectors and methods, wherein the protein sequence comprises at least one of (1) $Gly^{102}$, (2) $Phe^{124}$, (3) $Asn^{279}$, (4) $Gly^{393}$, (5) $Asn^{457}$, (6) $Asn^{463}$, (7) to $Tyr^{610}$ (8) $Val^{611}$, (9) $Ser^{733}$ and (10) $Val^{735}$. Preferably, the sequence comprises at least two of these amino acid residues, more preferably at least four, yet more preferably all of these amino acid residues.

In a second embodiment, the invention also provides a nucleic acid encoding a transporter protein having at least about 99.5% sequence identity with all or one to two contiguous portions of the amino acid sequence of SEQ ID 19 or with one to two continous portions of an amino acid sequence corresponding to the protein sequence of SEQ ID 19 except that it has one or more of the following substitutions (1) $Ser^{102}$ to Gly, (2) $Ser^{124}$ to Phe, (3) $Ile^{279}$ to Asn, (4) $Arg^{393}$ to Gly, (5) $Lys^{457}$ to Asn, (6) $Asp^{463}$ to Asn, (7) $Cys^{610}$ to Tyr, (8) $Ile^{611}$ to Val, (9) $Phe^{733}$ to Ser or (10) $Ile^{735}$ to Val, wherein the encoded protein has glycine transporter activity. Preferably, the contiguous sequences comprise at least about 600 amino acids, more preferably at least about 700 amino acids, more preferably at least about 750 amino acids. The invention also provides a vector comprising this nucleic acid. In one embodiment, the vector is effective to express a glycine transporter mRNA in at least one of a prokaryotic cell such as a bacterial cell or a eukaryotic cell. In another embodiment of the invention, the vector is effective to express the mRNA in at least one of a yeast cell, a mammalian cell or an avian cell.

The invention additionally provides a cell comprising a first extrinsically-derived nucleic acid according to the first embodiment or a second extrinsically-derived nucleic acid encoding a transporter protein having at least about 99.5% sequence identity with one to two contiguous portions of the protein sequence of SEQ ID 19 or of a sequence corresponding to the protein sequence of SEQ ID 19 except that it has one or more of the following substitutions (1) $Ser^{102}$ to Gly, (2) $Ser^{124}$ to Phe, (3) $Ile^{279}$ to Asn, (4) $Arg^{393}$ to Gly, (5) $Lys^{457}$ to Asn, (6) $Asp^{463}$ to Asn, (7) $Cys^{610}$ to Tyr, (8) $Ile^{611}$ to Val, (9) $Phe^{733}$ to Ser or (10) $Ile^{735}$ to Val, wherein the encoded protein has glycine transporter activity. In one embodiment, the cell expresses a glycine transporter from the nucleic acid. Preferably, the nucleic acid is functionally associated with a promoter that is operative in the cell. In an embodiment of the invention, the promoter is an inducible promoter.

The invention also provides a method of producing a glycine transporter comprising growing the cells described in the previous paragraph. This method can further comprise at least one of (a) isolating membranes from said cells, which membranes comprise the glycine transporter or (b) extracting a protein fraction from the cells, which fraction comprises the glycine transporter.

An embodiment of the invention provides a method for characterizing a bioactive agent for treatment of a nervous system disorder or condition or for identifying bioactive agents for treatment of a nervous system disorder or condition, the method comprising (a) providing a first assay composition comprising (i) a cell as described above or (ii) an isolated glycine transporter protein comprising the amino acid sequence encoded by the first or second extrinsically-derived nucleic acids described above, (b) contacting the first assay composition with the bioactive agent or a prospective bioactive agent, and measuring the amount of glycine transport exhibited by the assay composition. Preferably, the method further comprises comparing the amount of glycine transport exhibited by the first assay composition with the amount of glycine transport exhibited by a second such assay composition that is treated the same as the first assay composition except that it is not contacted with the bioactive agent or prospective bioactive agent. The method can be used for characterizing bioactive agents where the nervous system disorder or condition is one of the group consisting of (a) pain, (b)spasticity, (c) myoclonus, (d) muscle spasm, (e) muscle hyperactivity or (f) epilepsy. In a preferred embodiment, the spasticity for which the bioactive agent is characterized is associated with stroke, head trauma, neuronal cell death, multiple sclerosis, spinal cord injury, dystonia, Huntington's disease or amyotrophic lateral sclerosis.

The invention further provides a nucleic acid that hybridizes with the nucleic acid sequence of SEQ ID 18 or with a sequence that varies from the nucleic acid sequence of SEQ ID 18 by having one or more of the following substitutions (a) $T^6$ to C, (b) $A^{304}$ to G, (c) $C^{371}$ to T, (d) $C^{571}$ to T, (e) $T^{836}$ to A, (f) $A^{1116}$ to G, (g) $A^{1177}$ to G, (h) $G^{1371}$ to C, (i) $G^{1387}$ to A, (j) $G^{1829}$ to A, (k) $A^{1831}$ to G, (l) $G^{2103}$ to A, (m) $T^{2198}$ to C, or (n) $A^{2203}$ to G, under conditions of sufficient stringency to exclude hybridizations with (a) the sequence for a rat or mouse GlyT-2 transporter or (b) the sequence for a mammalian GlyT-1 transporter. Preferably, the nucleic acid sequence is at least about 18 nucleotides in length and has at least about 95% sequence identity with a sequence embedded in the nucleic acid sequence of SEQ ID 18 or a sequence that varies from the nucleic acid sequence of SEQ ID 18 by having one or more of the following substitutions (a) $T^6$ to C, (b) $A^{304}$ to G, (c) $C^{371}$ to T, (d) $C^{571}$ to T, (e) $T^{836}$ to A, (f) $A^{1116}$ to G, (g) $A^{1177}$ to G, (h) $G^{1371}$ to C, (i) $G^{1387}$ to A, (j) $G^{1829}$ to A, (k) $A^{1831}$ to G, (l) $G^{2103}$ to A, (m) $T^{2198}$ to C, or (n) $A^{2203}$ to G. Preferably the nucleic acid sequence is at least about 40 nucleotides in length, more preferably at least about 100 nucleotides in length. Preferably the nucleic acid sequence has at least about 97% sequence identity with the above-recited reference sequence, more preferably 99% sequence identity. Preferably, the nucleic acid is a PCR primer and the stringent conditions are PCR conditions effective to amplify a human GlyT-2 sequence but not to amplify (a) the sequence for a rat or mouse GlyT-2 transporter or (b) the sequence for a mammalian GlyT-1 transporter.

Further, the invention provides a nucleic acid of at least about 18 nucleotides in length comprising a contiguous sequence from the coding or noncoding strand of a human GlyT-2 gene or cDNA, wherein the contiguous sequence has at least 1 sequence difference when compared with the rat GlyT-2 gene sequence that aligns with the contiguous sequence. Preferably the nucleic acid sequence is at least about 40 nucleotides in length, more preferably at least about 100 nucleotides in length. Preferably, the contiguous sequence has at least two differences, more preferably 3 differences when compared with the rat GlyT-2 gene sequence that aligns with the contiguous sequence.

Still further, the invention provides an antisense molecule comprising a contiguous sequence from a coding or non-coding strand of a human gene or cDNA for GlyT-2 which is effective when administered to a cell, tissue, organ or animal to reduce the expression of GlyT-2 in the cell or in a cell of the tissue, organ or animal, wherein the contiguous sequence has at least 1 sequence difference when compared with the rat GlyT-2 gene sequence that aligns with said contiguous sequence. Preferably, the contiguous sequence has at least two differences, more preferably 3 differences when compared with the rat GlyT-2 gene sequence that aligns with the contiguous sequence. The phrase "antisense molecule," is used herein to refer to a molecule designed to bind genomic DNA or mRNA to interfere in transcription or translation, including interfering with mRNA stability. Preferably, the contiguous sequence is at least about 15 nucleotides in length. Preferably, the contiguous stretch is included in the coding or non-coding strand of the nucleic acid sequence of SEQ ID 18 or of a sequence that varies from the nucleic acid sequence of SEQ ID 18 by having one or more of the following substitutions (a) $T^6$ to C, (b) $A^{304}$ to G, (c) $C^{371}$ to T, (d) $C^{571}$ to T, (e) $T^{836}$ to A, (f) $A^{1116}$ to G, (g) $A^{1177}$ to G, (h) $G^{1371}$ to C, (i) $G^{1387}$ to A, (j) $G^{1829}$ to A, (k) $A^{1831}$ to G, (l) $G^{2103}$ to A, (m) $T^{2198}$ to C, or (n) $A^{2203}$ to G. Preferably, the contiguous stretch is in the coding or non-coding strand of the nucleic acid sequence of SEQ ID 18. The invention further provides an expression vector comprising such an antisense molecule.

The invention also provides a method of reducing GlyT-2 expression in a tissue or cell comprising applying to the tissue or cell a GlyT-2 expression reducing effective amount of such an antisense molecule or a GlyT-2 expression reducing effective amount of an expression vector for expressing such an antisense molecule in a tissue or cell. Alternatively, the invention provides a method of treating a nervous system disorder or condition comprising applying to a tissue or cell of a human patient a nervous system disorder or condition treating effective amount of such an antisense molecule or a nervous system disorder or condition treating effective amount of an expression vector for expressing such an antisense molecule in a tissue or cell.

Further, the invention provides a method for detecting whether an animal has autoimmune antibodies against a glycine transporter, the method comprising contacting an antibody preparation from the animal or a body fluid from the animal with a polypeptide antigen comprising a glycine transporter or derived from the glycine transporter. Preferably, the polypeptide antigen comprises a contiguous sequence encoded by the protein sequence of SEQ ID 19 or with a sequence corresponding to the protein sequence of SEQ ID 19 except that it has one or more of the following substitutions (1) $Ser^{102}$ to Gly, (2) $Ser^{124}$ to Phe, (3) $Ile^{279}$ to Asn, (4) $Arg^{393}$ to Gly, (5) $Lys^{457}$ to Asn, (6) $Asp^{463}$ to Asn, (7) $Cys^{610}$ to Tyr, (8) $Ile^{611}$ to Val, (9) $Phe^{733}$ to Ser or (10) $Ile^{735}$ to Val. Preferably, the contiguous sequence is at least about six amino acids in length, more preferably at least about ten amino acids in length, still more preferably at least about fifteen amino acids in length. In one embodiment of the invention, the peptide antigen is selective for antibodies against either a GlyT-1 transporter or a a GlyT-2 transporter.

BRIEF DESCRIPTION OF THE DRAWINGS

FIGS. 3A–E show a comparison between the nucleic acid sequence of SEQ ID 18 and the rat GlyT-2 of SEQ ID NO:26 sequence.

FIGS. 4A–B show a comparison between the amino acid sequence of SEQ ID 19 and the rat GlyT-2 of SEQ ID NO:27 sequence.

DEFINITIONS

Figure 1:
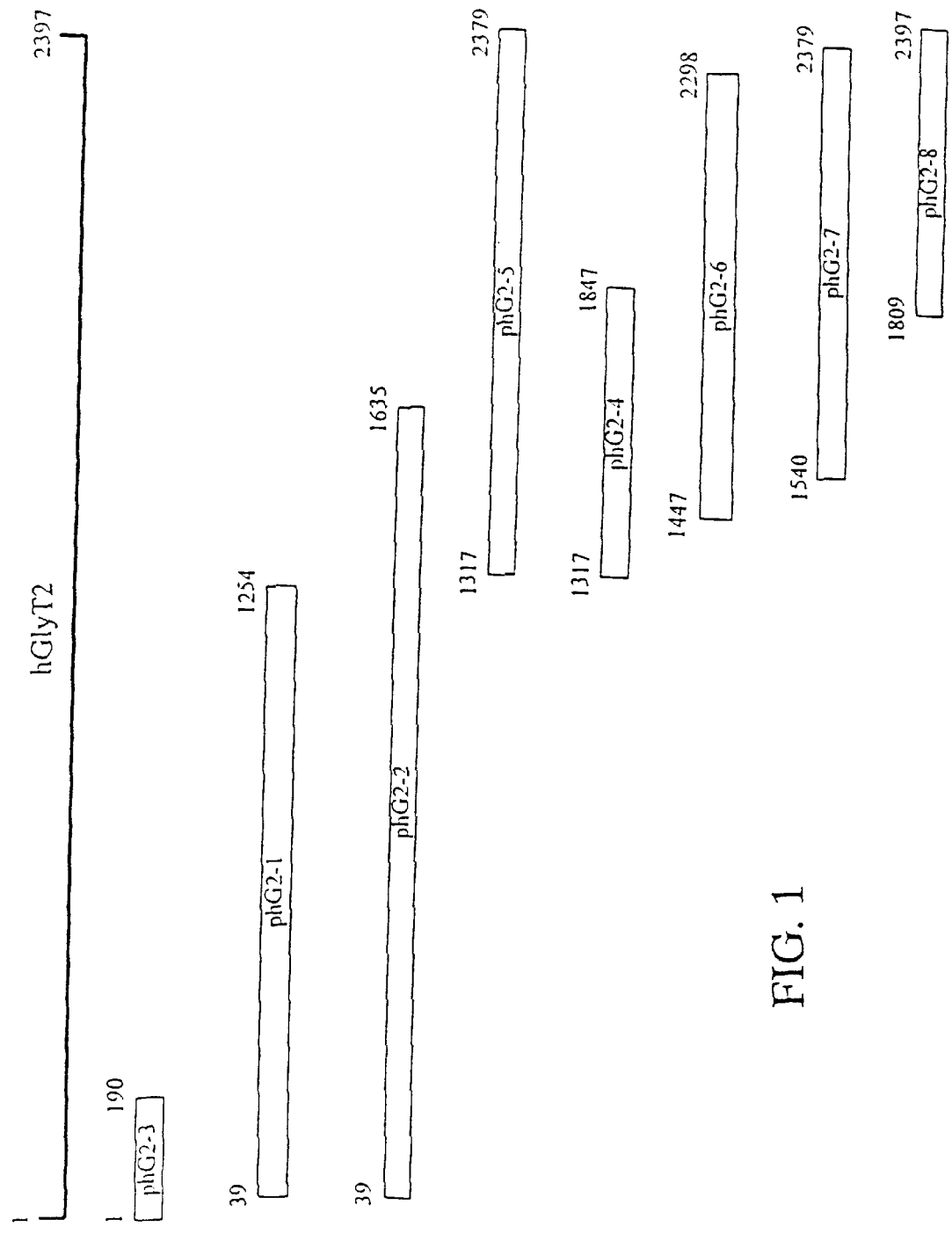
FIG. 1 shows the alignment of several gene fragments of the human GlyT-2 gene.

For the purposes of this application, the following terms shall have the meaning set forth below.

Bioactive agent

A bioactive agent is a substance such as a chemical that can act on a cell, virus, tissue, organ or organism, including but not limited to drugs (i.e. pharmaceuticals) to create a change in the functioning of the cell, virus, organ or organism. Preferably, the organism is a mammal, more preferably a human. In a preferred embodiment of the invention, the method of identifying bioactive agents of the invention is applied to organic molecules having molecular weight of about 1500 or less.

extrinsically-derived nucleic acid

Extrinsically-derived nucleic acids are nucleic acids found in a cell that were introduced into the cell, a parent or ancestor of the cell, or a transgenic animal from which the cell is derived through a recombinant technology.

extrinsic promoter functionally associated with a nucleic acid

An extrinsic promoter for a protein-encoding nucleic acid is a promoter distinct from that used in nature to express a nucleic acid for that protein. A promoter is functionally associated with the nucleic acid if in a cell that is compatable with the promoter the promoter can act to allow the transcription of the nucleic acid.

nucleic acid-specific property

Nucleic acid-specific properties are properties that can be used to distinguish differing nucleic acid molecules. Such properties include, without limitation (i) the nucleotide sequence of all or a portion of the molecule, (ii) the size of the molecule, for instance determined by electrophoresis, (iii) the fragmentation pattern generated by treatment with chemicals that fragment nucleic acid or generated by nucleases and (iv) the ability of the molecule or fragments thereof to hybridize with defined nucleic acid probes.

prospective agent

Prospective agents are substances which are being tested by the screening method of the invention to determine if they affect glycine transport.

DETAILED DESCRIPTION OF THE INVENTION

The GlyT-2 nucleic acid sequence of SEQ ID 18 or the corresponding encoded protein sequence of SEQ ID 19, are human relatives of the rat GlyT-2 sequence reported in Liu et al., *J. Biol. Chem.* 268: 22802–22808, 1992. SEQ ID 21, the GlyT-2 protein sequence encoded by the nucleic acid sequence of SEQ ID 19, differs from the amino acid sequence of SEQ ID 19, most likely reflecting variant forms of human GlyT-2. Additional sequences set forth in SEQ IDs 1–25 reflect still further variations. These variations primarily arise from the use of cDNA from pooled mRNA for several donors to generate the clones. In total, the various human GlyT-2-derived nucleic acids that have been isolated reveal the following sequence variations:

| Nucleotide variations | Encoded Amino Acid Variations | Corresponding Amino Acid in Rat |
|---|---|---|
| A$\underline{T}^6$T (from SEQ ID 18) to A$\underline{C}$T (from SEQ ID 3) | NONE (Asp$^2$ to Asp) | Asp |
| $\underline{A}^{304}$GC (from SEQ ID 18) to $\underline{G}$GC (from SEQ ID 20) | Ser$^{102}$ to Gly | Ser |
| T$\underline{T}^{371}$T (from SEQ ID 20) to T$\underline{C}$T (from SEQ ID 18) | Phe$^{124}$ to Ser | Ala |
| $\underline{C}^{571}$GA (from SEQ ID 18) to $\underline{T}$GA (from SEQ ID 7) | Arg$^{191}$ to STOP | Arg |
| A$\underline{T}^{836}$C (from SEQ ID 18) to A$\underline{A}$C (from SEQ ID 20) | Ile$^{279}$ to Asn | Ile |
| GA$\underline{G}^{1116}$ (from SEQ ID 20) to GA$\underline{A}$ (from SEQ ID 18) | NONE (Glu$^{372}$ to Glu) | Glu |
| $\underline{G}^{1177}$GG (from SEQ ID 5) to $\underline{A}$GG (from SEQ ID 18) | Gly$^{393}$ to Arg | Arg |
| AA$\underline{C}^{1371}$ (from SEQ ID 10) to AA$\underline{G}$ (from SEQ ID 18) | Asn$^{457}$ to Lys | Lys |
| $\underline{G}^{1387}$AT (from SEQ ID 18) to $\underline{A}$AT (from SEQ ID 12) | Asp$^{463}$ to Asn | Asp |
| T$\underline{G}^{1829}$C (from SEQ ID 18) to T$\underline{A}$C (from SEQ ID 22) | Cys$^{610}$ to Tyr | Cys |
| $\underline{A}^{1831}$TT (from SEQ ID 18) to $\underline{G}$TT (from SEQ ID 20) | Ile$^{611}$ to Val | Ile |
| GA$\underline{G}^{2103}$ (from SEQ ID 18) to GA$\underline{A}$ (from SEQ ID 24) | NONE (Glu$^{701}$ to Glu) | Glu |
| T$\underline{T}^{2198}$T (from SEQ ID 18) to T$\underline{C}$T (from SEQ ID 24) | Phe$^{733}$ to Ser | Phe |
| $\underline{A}^{2203}$TA (from SEQ ID 18) to $\underline{G}$TA (from SEQ ID 22) | Ile$^{735}$ to Val | Ile |

Irrespective of the source of this variation, the point variations in peptide sequence, excepting the insertion of the stop codon, are believed not to adversely affect the functioning of GlyT-2. The GlyT-2 protein sequence of SEQ ID 19 is most preferred.

The above-described variations primarily reflect sequence variations between human individuals. The material used to generate the nucleic acid sequences described above comprised pools from either twenty-six or ninety-two individuals, depending on the particular nucleic acid sequence. The use of pooled source material, together with the prevalence of silent or conservative substitutions, support the conclusion that the variations are reflective of human-derived variations rather than mutations generated by the amplification reactions.

The relationship between the human nucleotide sequence of SEQ ID 18 and the rat nucleotide sequence for GlyT-2, and between the protein sequences that they encode, is as set forth in the tables below. The relatedness values set forth in these tables was determined using the FASTA computer program described by Pearson and Lipman, *Proc. Natl. Acad. Sci. USA* 85: 2444–2448, 1988.

| Nucleotide Sequence (numbered as in SEQ ID 18) | Percent Identity |
|---|---|
| nt 1–2397 (whole sequence) | 89 |
| nt 1–600 | 82.5 |
| nt 60–170 | 78 |
| nt 600–2397 | 91.2 |

| Amino Acid Sequence (numbered as in SEQ ID 19) | Percent Identity |
|---|---|
| aa 1–797 | 94.4 |
| aa 1–150 | 77.1 |
| aa 1–200 | 80.3 |
| aa 150–797 | 98.5 |
| aa 200–797 | 99.2 |

Nucleic Acid—encoding glycine transporter

To construct non-naturally occurring glycine transporter-encoding nucleic acids, the native sequences can be used as a starting point and modified to suit particular needs. For instance, the sequences can be mutated to incorporate useful restriction sites. See Maniatis et al. *Molecular Cloning, a Laboratory Manual* (Cold Spring Harbor Press, 1989). Such restriction sites can be used to create "cassettes", or regions of nucleic acid sequence that are facilely substituted using restriction enzymes and ligation reactions. The cassettes can be used to substitute synthetic sequences encoding mutated glycine transporter amino acid sequences. Alternatively, the glycine transporter-encoding sequence can be substantially or fully synthetic. See, for example, Goeddel et al., *Proc. Natl. Acad. Sci. USA*, 76, 106–110, 1979. For recombinant expression purposes, codon usage preferences for the organism in which such a nucleic acid is to be expressed are advantageously considered in designing a synthetic glycine transporter-encoding nucleic acid. For example, a nucleic acid sequence incorporating prokaryotic codon preferences can be designed from a mammalian-derived sequence using a software program such as Oligo-4, available from National Biosciences, Inc. (Plymouth, Minn).

The nucleic acid sequence embodiments of the invention are preferably deoxyribonucleic acid sequences, preferably double-stranded deoxyribonucleic acid sequences. However, they can also be ribonucleic acid sequences.

Numerous methods are known to delete sequence from or mutate nucleic acid sequences that encode a protein and to confirm the function of the proteins encoded by these deleted or mutated sequences. Accordingly, the invention also relates to a mutated or deleted version of a human nucleic acid sequence that encodes a protein that retains the ability to bind specifically to glycine and to transport glycine across a membrane. These analogs can have N-terminal, C-terminal or internal deletions, so long as GlyT-2 function is retained. The remaining human GlyT-2 protein sequence will preferably have no more than about 4 amino acid variations, preferably no more than 2 amino acid variations, more preferably no more than 1 amino acid variation, relative to the protein sequence of SEQ ID 19 or with a sequence corresponding to the protein sequence of SEQ ID 19 except that it has one or more of the following substitutions (1) $Ser^{102}$ to Gly, (2) $Ser^{124}$ to Phe, (3) $Ile^{279}$ to Asn, (4) $Arg^{393}$ to Gly, (5) $Lys^{457}$ to Asn, (6) $Asp^{463}$ to Asn, (7) $Cys^{610}$ to Tyr, (8) $Ile^{611}$ to Val, (9) $Phe^{733}$ to Ser or (10) $Ile^{735}$ to Val. More preferably, the variations are relative to the protein sequence of SEQ ID 18. The point variations are preferably conservative point variations. Preferably, the analogs will have at least about 96% sequence identity, preferably at least about 97%, more preferably at least about 98%, still more preferably at least about 99%, yet still more preferably at least about 99.5%, to the protein sequence of SEQ ID 19 or with a sequence corresponding to the protein sequence of SEQ ID 19 except that it has one or more of the following substitutions (1) $Ser^{102}$ to Gly, (2) $Ser^{124}$ to Phe, (3) $Ile^{279}$ to Asn, (4) $Arg^{393}$ to Gly, (5) $Lys^{457}$ to Asn, (6) $Asp^{463}$ to Asn, (7) $Cys^{610}$ to Tyr, (8) $Ile^{611}$ to Val, (9) $Phe^{733}$ to Ser or (10) $Ile^{735}$ to Val. More preferably, the variations are relative to the protein sequence of SEQ ID 18.

Mutational and deletional approaches can be applied to all of the nucleic acid sequences of the invention that express human GlyT-2 proteins. As discussed above, conservative mutations are preferred. Such conservative mutations include mutations that switch one amino acid for another within one of the following groups:

1. Small aliphatic, nonpolar or slightly polar residues: Ala, Ser, Thr, Pro and Gly;
2. Polar, negatively charged residues and their amides: Asp, Asn, Glu and Gln;
3. Polar, positively charged residues: His, Arg and Lys;
4. Large aliphatic, nonpolar residues: Met, Leu, Ile, Val and Cys; and
5. Aromatic residues: Phe, Tyr and Trp.

A preferred listing of conservative variations is the following:

| Original Residue | Variation |
|---|---|
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

The types of variations selected may be based on the analysis of the frequencies of amino acid variations between homologous proteins of different species developed by Schulz et al., *Principles of Protein Structure,* Springer-Verlag, 1978, on the analyses of structure-forming potentials developed by Chou and Fasman, *Biochemistry* 13, 211, 1974 and Adv. Enzymol, 47, 45–149, 1978, and on the analysis of hydrophobicity patterns in proteins developed by Eisenberg et al., *Proc. Natl. Acad. Sci. USA* 81, 140–144, 1984; Kyte & Doolittle; *J. Molec. Biol.* 157, 105–132, 1981, and Goldman et al., *Ann. Rev. Biophys. Chem.* 15, 321–353, 1986. All of the references of this paragraph are incorporated herein in their entirety by reference.

Since the ten identified point variations which create amino acid substitutions between the various human GlyT-2 mRNAs identified herein are believed to be useful in creating functional GlyT-2, proteins incorporating all combinations of these point variations are believed to be functional. These variations are within the invention.

For the purposes of this application, a nucleic acid of the invention is "isolated" if it has been separated from other macromolecules of the cell or tissue from which it is derived. Preferably, the composition containing the nucleic acid is at least about 10-fold enriched, with respect to nucleic acid content, over the composition of the source cells. Preferably, the nucleic acid is substantially pure, meaning purity of at least about 60% w/w with respect to other nucleic acids, more preferably about 80%, still more preferably about 90%, yet more preferably about 95%.

Hybridization Probes

It will be recognized that many deletional or mutational analogs of nucleic acid sequences for a glycine transporter will be effective hybridization probes for glycine transporter-encoding nucleic acid. Accordingly, the invention relates to nucleic acid sequences that hybridize with such glycine transporter-encoding nucleic acid sequences under stringent conditions. Preferably, the nucleic acid sequence hybridizes with the nucleic acid sequence of of SEQ ID 18 or with a nucleic acid sequence that varies therefrom by one or more of the following substitutions (a) $T^6$ to C, (b) $A^{304}$ to G, (c) $C^{371}$ to T, (d) $C^{571}$ to T, (e) $T^{836}$ to A, (f) $A^{1116}$ to G, (g) $A^{1177}$ to G, (h) $G^{1371}$ to C, (i) $G^{1387}$ to A, (j) $G^{1829}$ to A, (k) $A^{1831}$ to G, (l) $G^{2103}$ to A, (m) $T^{2198}$ to C, or (n) $A^{2203}$ to G.

"Stringent conditions" refers to conditions that allow for the hybridization of substantially related nucleic acid sequences. For instance, such conditions will generally allow hybridization of sequence with at least about 85% sequence identity, preferably with at least about 90% sequence identity, more preferably with at least about 95% sequence identity. Such hybridization conditions are described by Sambrook et al., *Molecular Cloning: A Laboratory Manual*, 2nd ed., Cold Spring Harbor Press, 1989. Hybridization conditions and probes can be adjusted in well-characterized ways to achieve selective hybridization of human-derived probes.

Nucleic acid molecules that will hybridize to a glycine transporter-encoding nucleic acid under stringent conditions can be identified functionally, using methods outlined above, or by using for example the hybridization rules reviewed in Sambrook et al., *Molecular Cloning: A Laboratory Manual*, 2nd ed., Cold Spring Harbor Press, 1989.

Without limitation, examples of the uses for hybridization probes include: histochemical uses such as identifying tissues that express the human GlyT-2 transporter; measuring mRNA levels, for instance to identify a sample's tissue type or to identify cells that express abnormal levels of glycine transporter; and detecting polymorphisms in the glycine transporter gene. RNA hybridization procedures are described in Maniatis et al. *Molecular Cloning, a Laboratory Manual* (Cold Spring Harbor Press, 1989).

PCR Primers

Rules for designing polymerase chain reaction ("PCR") primers are now established, as reviewed by PCR *Protocols*, Cold Spring Harbor Press, 1991. Degenerate primers, i.e., preparations of primers that are heterogeneous at given sequence locations, can be designed to amplify nucleic acid sequences that are highly homologous to, but not identical to, a human GlyT-2 nucleic acid. Strategies are now available that allow for only one of the primers to be required to specifically hybridize with a known sequence. See, Froman et al., *Proc. Natl. Acad. Sci. USA* 85: 8998, 1988 and Loh et al. *Science* 243: 217, 1989. For example, appropriate nucleic acid primers can be ligated to the nucleic acid sought to be amplified to provide the hybridization partner for one of the primers. In this way, only one of the primers need be based on the sequence of the nucleic acid sought to be amplified.

PCR methods of amplifying nucleic acid will utilize at least two primers. One of these primers will be capable of hybridizing to a first strand of the nucleic acid to be amplified and of priming enzyme-driven nucleic acid synthesis in a first direction. The other will be capable of hybridizing the reciprocal sequence of the first strand (if the sequence to be amplified is single stranded, this sequence will initially be hypothetical, but will be synthesized in the first amplification cycle) and of priming nucleic acid synthesis from that strand in the direction opposite the first direction and towards the site of hybridization for the first primer. Conditions for conducting such amplifications, particularly under preferred stringent hybridization conditions, are well known. See, for example, PCR *Protocols*, Cold Spring Harbor Press, 1991.

Vectors

A suitable expression vector is capable of fostering expression of the included GlyT-2 encoding DNA in a host cell, which can be eukaryotic, fungal, or prokaryotic. Suitable expression vectors include pRc/CMV (Invitrogen, San Diego, Calif.), pRc/RSV (Invitrogen), pcDNA3 (Invitrogen), Zap Express Vector (Stratagene Cloning Systems, LaJolla, Calif.); pBk/CMV or pBk-RSV vectors (Stratagene), Bluescript II SK±Phagemid Vectors (Stratagene), LacSwitch (Stratagene), pMAM and pMAM neo (Clontech, Palo Alto, Calif.), pKSV10 (Pharmacia, Piscataway, N.J.), pCRscript (Stratagene) and pCR2.1 (Invitrogen), among others. Useful yeast expression systems include, for example, pYEUra3 (Clontech). Useful baculovirus vectors include several viral vectors from Invitrogen (San Diego, Calif.) such as pVL1393, pVL1392, pBluBac2, pBluBacHis A, B or C, and pbacPAC6 (from Clontech).

Cells

In one embodiment of the invention, the transporter is preferably expressed in a mammalian cell line, preferably a transformed cell line with an established cell culture history. In this embodiment, particularly preferred cell lines include COS-1, COS-7, LM(tk$^-$), HeLa, HEK293, CHO, Rat-1 and NIH3T3. Other preferred cells include avian cells such as QT-6 cells. Other cells that can be used include insect cells such as drosophila cells, fish cells, amphibian cells and reptilian cells.

In another embodiment, the transporter is expressed in a cell line that is more inexpensively maintained and grown than are mammalian cell lines, such as a bacterial cell line or a yeast cell line.

Isolated Glycine Transporter

The invention also provides for the human GlyT-2 proteins encoded by any of the nucleic acids of the invention preferably in a purity of at least about 80% with respect to proteins, preferably 90%, more preferably 95%. The purities are achieved, for example, by applying protein purification methods, such as those described below, to a lysate of a recombinant cell according to the invention.

The human GlyT-2 variants of the above paragraphs can be used to create organisms or cells that produce human GlyT-2 activity. Purification methods, including associated molecular biology methods, are described below.

Method of Producing Glycine Transporter

One simplified method of isolating polypeptides synthesized by an organism under the direction of one of the nucleic acids of the invention is to recombinantly express a fusion protein wherein the fusion partner is facilely affinity purified. For instance, the fusion partner can be glutathione S-transferase, which is encoded on commercial expression vectors (e.g., vector pGEX4T3, available from Pharmacia, Piscataway, N.J.). The fusion protein can then be purified on a glutathione affinity column (for instance, that available from Pharmacia, Piscataway, N.J.). Of course, the recombinant polypeptides can be affinity purified without such a fusion partner using an appropriate antibody that binds to GlyT-2. Methods of producing such antibodies are available to those of ordinary skill in light of the ample description herein of GlyT-2 expression systems and known antibody production methods. See, for example, Ausubel et al., *Short Protocols in Molecular Biology*, John Wiley & Sons, New York, 1992. If fusion proteins are used, the fusion partner can be removed by partial proteolytic digestion approaches that preferentially attack unstructured regions such as the linkers between the fusion partner and GlyT-2. The linkers can be designed to lack structure, for instance using the rules for secondary structure forming potential developed, for instance, by Chou and Fasman, *Biochemistry* 13, 211, 1974 and Chou and Fasman, *Adv. in EnzymoL.* 47, 45–147, 1978. The linker can also be designed to incorporate protease target amino acids, such as, arginine and lysine residues, the amino acids that define the sites cleaved by trypsin. To create the linkers, standard synthetic approaches for making oligonucleotides can be employed together with standard subcloning methodologies. Other fusion partners besides GST can be used. Procedures that utilize eukaryotic cells, particularly mammalian cells, are preferred since these cells will post-translationally modify the protein to create molecules highly similar to or functionally identical to native proteins.

Additional purification techniques can be applied, including without limitation, preparative electrophoresis, FPLC (Pharmacia, Uppsala, Sweden), HPLC (e.g., using gel filtration, reverse-phase or mildly hydrophobic columns), gel filtration, differential precipitation (for instance, "salting out" precipitations), ion-exchange chromatography and affinity chromatography.

Because GlyT-2 is a membrane protein, which by analogy to related transporter proteins is believed to have twelve transmembrane sequences, isolation methods will often utilize detergents, generally non-ionic detergents, to maintain the appropriate secondary and tertiary structure of the protein. See, for example, Lopez-Corcuera et al., *J. Biol Chem.* 266: 24809–24814, 1991. For a description of methods for re-integrating a solubilized transporter into a membrane, see Lopez-Corcuera et al., *J. Biol. Chem.* 266: 24809–24814, 1991.

The isolation of GlyT-2 can comprise isolating membranes from cells that have been transformed to express GlyT-2. Preferably, such cells express GlyT-2 in sufficient copy number such that the amount of GlyT-2 in a membrane fraction is at least about 10-fold higher than that found in comparable membranes from cells that naturally express GlyT-2, more preferably the amount is at least about 100-fold higher.

Preferably, the protein is substantially pure, meaning a purity of at least 60% w/w with respect to other proteins. For the purposes of this application, GlyT-2 is "isolated" if it has been separated from other proteins or other macromolecules of the cell or tissue from which it is derived. Preferably, the composition containing GlyT-2 is at least about 10-fold enriched, preferably at least about 100-fold, with respect to protein content, over the composition of the source cells.

Expression of GlyT-2 by RNA Insertion

It will be recognized that human GlyT-2 can be expressed by the simple method of inserting mRNA into a cell. RNA for these uses can be prepared by sub-cloning the nucleic acid encoding a protein with GlyT-2 activity into a vector containing a promoter for high efficiency in vitro transcription, such as a SP6 or T7 RNA polymerase promoter. RNA production from the vector can be conducted, for instance, with the method described in Ausubel et al., *Short Protocols in Molecular Biology*, John Wiley & Sons, New York, 1992, pp. 10–63 to 10–65. Insertion of RNA into Xenopus-derived oocytes is described, for instance, in Liu et al. *FEBS Letters* 305: 110–114, 1992 and Bannon et al., *J. Neurochem.* 54: 706–708, 1990.

Alternatively, it will be recognized that human GlyT-2 can be expressed by the simple method of inserting mRNA into an in vitro translation system, which can be a membrane-containing translation system. Expression of proteins in vitro is described, for instance, in Ausubel et al., *Short Protocols in Molecular Biology*, John Wiley & Sons, New York, 1992, pp. 10–63 to 10–65. See, also, Guastella et al., *Science* 249: 1303–1306, 1990 (in vitro expression of a transporter). The use of subcellular membranous material to produce membrane proteins in vitro is described in Walter and Blobel, *Meth. Enzymol.* 96: 84, 1983 (for rabbit reticulocyte translation system) and Spiess and Lodish, *Cell* 44: 177, 1986 (for wheat germ translation system).

Method of Characterizing or Identifying agent

A method for the analysis of or screening for a bioactive agent for treatment of a disease or condition associated with a nervous system disorder or condition comprises culturing separately first and second cells, wherein the first and second cells are preferably of the same species, more preferably of the same strain thereof, and comprise an exogenous nucleic acid encoding a glycine transporter as described herein. The nervous system disorders or conditions for which the agent can be used for treatment include, but are not limited to, (a) pain, (b) myoclonus, (c) muscle spasm, (d) muscle hyperactivity, (e) epilepsy or (f) spasticity such as that associated with stroke, head trauma, neuronal cell death, multiple sclerosis, spinal cord injury, dystonia, Huntington's disease or amyotrophic lateral sclerosis. In this method, the first cell is contacted with the bioactive agent or a prospective agent, which is preferably a compound, such as a peptide or an organic compound in the presence of glycine, which preferably incorporates a radioisotope, such as $^3$H or $^{14}$C. The contacted first cell is then tested for enhancement or inhibition of glycine transport into the first cell as compared to glycine transport into the second cell that was not contacted with the compound (i.e., the control cell). Such analysis or screening preferably includes activities of finding, learning, discovering, determining, identifying, or ascertaining.

Alternatively, the assay can utilize a composition comprising an isolated GlyT-2 transporter in place of cells. Preferably, such preparation of isolated transporter will comprise vesicles of membrane or lipid bilayer, which vesicles have an inside and an outside across which transport can be measured. See, for example, Kanner, *Biochemistry* 17: 1207–1211, 1978.

A bioactive agent is an enhancer of glycine transport uptake if at the end of the test the amount of intracellular or intravesicle glycine is greater in the agent-contacted composition than in the non-agent-contacted composition; conversely, a bioactive agent is an inhibitor of glycine transport if the amount of intracellular or intravesicle glycine is greater in the non-agent-contacted composition as compared to the other. Preferably, the difference in glycine uptake between a tested first composition and a control second composition is at least about two-fold; more preferably, the difference is at least about five-fold; most preferably, the difference is at least about ten-fold or greater.

A bioactive agent that is an inhibitor or an enhancer with respect to the GlyT-2 transporter may have a neutral or opposite effect with another glycine transporter, such as one of the GlyT-1 transporters. Preferred bioactive agents have specificity to enhance or inhibit the GlyT-2 transporter and have neutral or negligible effect on other glycine transporters. Preferably, a bioactive agent has at least an order of magnitude greater potency, reflected in a concentration dependent parameter such as the $IC_{50}$ value, in inhibiting or activating glycine uptake mediated by the GlyT-2 transporter as compared to its effect on the second glycine transporter. More preferred agents have greater potencies of at least about 100-fold for one of the glycine transporters as compared to the other.

The bioactive agent can be any compound, material, composition, mixture, or chemical, that can be presented to a glycine transporter in a form that allows for the agent to diffuse so as to contact the transporter. Such bioactive agents include but are not limited to polypeptides preferably of two up to about 25 amino acids in length, more preferably from two to about ten, yet more preferably from two to about five amino acids in length. Other suitable bioactive agents in the context of the present invention include small organic compounds, preferably of molecular weight between about 100 daltons and about 5,000 daltons, and are composed of such functionalities as alkyl, aryl, alkene, alkyne, halo, cyano and other groups, including heteroatoms or not. Such organic compounds can be carbohydrates, including simple sugars, amino or imino acids, nucleic acids, steroids, and others. The chemicals tested as prospective agents can be prepared using combinatorial chemical processes known in the art or conventional means for chemical synthesis. Preferably, bioactive agents are useful as drugs for treatment of nervous system disorders or conditions.

Some compounds that inhibit GlyT-1 or GlyT-2 mediated transport also bind to the glycine binding site on the strychnine-sensitive receptor, or to the glycine binding site on the NMDA receptor. Such binding to the strychnine-sensitive receptor can be identified by a binding assay whereby, for example, radiolabeled strychnine is placed in contact with a preparation of strychnine-sensitive receptors, such as can be prepared from a membrane fraction from spinal cord or brain stem tissue. A membrane fraction can be prepared using conventional means, including, for example, methods of homogenization and centrifugation.

Such binding to the NMDA receptor can be identified by a binding assay whereby, for example, radiolabeled glycine is placed in contact with a preparation of NMDA receptors, such as can be prepared from a membrane fraction from neuronal cells or brain tissue. Grimwood et al., *Molec. Pharmacol.*, 41:923–930, 1992. The NMDA receptors located in such membranes are treated using mild detergent, such as about 0.1% to about 0.5% saponin, to remove any endogenous glycine or glutamate.

The ligand used in such a binding assay is radiolabeled with any detectable isotope, such as radioactive isotopes of carbon or hydrogen. Specific binding of the radiolabeled ligand is then determined by subtracting the radioactivity due to non-specific binding from that which is due to total (i.e., specific and non-specific) binding of the radiolabeled ligand. The radioactivity due to non-specific binding is determined by measuring the amount of radiolabel associated with a strychnine-sensitive or NMDA receptor-containing membrane fraction that has been contacted with both radiolabeled ligand and a significant excess of non-radiolabeled ligand, such as a 100-fold excess. The radioactivity due to total binding of the radiolabeled ligand is determined by measuring the amount of radiolabel bound to the receptor preparation in the absence of non-radiolabeled ligand. For the NMDA receptor, one can also measure binding to the glycine site on the receptor using labeled analogs of amino acids, such as, for example, dichlorokynurenic acid or L-689,560. See, for example, Grimwood et al., *Molecular Pharmacol,* 49: 923–930, 1992.

Functional ion-flux assays are used to measure the effect of compounds identified by the present invention in enhancing or inhibiting calcium flux (for NMDA receptor preparations) or chloride flux (for strychnine-sensitive receptor preparations). This test is performed on cell cultures that have membrane-bound NMDA receptors or strychninesensitive receptors and glycine transporters. Such cells include neuronal cells generally, including those of the brain stem and spinal cord, and cell lines derived therefrom, and any other cell that has been induced or transfected to express NMDA receptors or strychnine-sensitive receptors. Calcium used in such a test is commonly the $^{45}$Ca isotope, although other calcium measuring techniques can be used as well, such as calcium-associated fluorescence, which can be fluorescence associated with a calcium chelator, and the like. Chloride used in such a test usually includes the isotope $^{36}$Cl. By whatever method the calcium or chloride is monitored, ion flux can be enhanced or inhibited as a result of the discrete addition of a bioactive agent of the present invention. An advantage of this system is that it allows one to monitor the net effect on NMDA receptor or strychnine-sensitive receptor function of a compound that interacts with both the glycine site on a receptor and on a glycine transporter.

GlyT-2 inhibitors that are also strychnine-sensitive receptor agonists act in the above-described indications by increasing glycine concentrations at the strychnine-sensitive receptor-expressing synapse via inhibition of the glycine transporter, and via directly enhancing strychnine-sensitive receptor activity. Glycine transporter inhibitors that are also strychnine-sensitive receptor antagonists can nonetheless retain activity in treating these indications, if the increase in glycine due to glycine transport inhibition prevails over the strychnine-sensitive receptor antagonism. Where the strychnine-sensitive receptor antagonist activity prevails over the effect of increased extracellular glycine resulting from inhibition of the glycine transporter, these compounds are useful in treating conditions associated with decreased muscle activity such as myasthenia gravis.

As discussed above, the bioactive agents of the invention can have a number of pharmacological actions. The relative effectiveness of the compounds can be assessed in a number of ways, including the following:

1. Comparing the activity mediated through GlyT-1 and GlyT-2 transporters. This testing identifies bioactive agents (a) that are more active against GlyT-1 transporters and thus more useful in treating or preventing schizophrenia, increasing cognition and enhancing memory or (b) that are more active against GlyT-2 transporters and thus more useful in treating or preventing epilepsy, pain or spasticity.

2. Testing for strychnine-sensitive receptor or NMDA receptor binding. This test establishes whether there is sufficient binding at this site to warrant further examination of the pharmacological effect of such binding.

3. Testing the activity of the compounds in enhancing or diminishing ion fluxes in primary tissue culture, for example chloride ion fluxes mediated by strychnine-sensitive receptors or calcium ion fluxes mediated by NMDA receptors. A bioactive agent that increases ion flux either (a) has little or no antagonist activity at the strychnine-sensitive receptor and should not affect the potentiation of glycine activity through GlyT-2 transporter inhibition or (b), if marked increases are observed over results with comparative GlyT-2 inhibitors that have little direct interaction with strychnine-sensitive receptors, then the agent is a receptor agonist.

In some cases, the agent analysis method of the invention will be used to characterize whether a bioactive agent is useful in treating an indication in which NMDA receptors and GlyT-1 transporters are implicated. In this case, generally, a lower measure of activity with respect to strychnine-sensitive receptors and GlyT-2 transporters is more desirable.

Antisense Therapies

One aspect of the present invention is directed to the use of "antisense" nucleic acid to treat neurological indications such as those identified above. The approach involves the use of an antisense molecule designed to bind mRNA coding for a GlyT-2, thereby stopping or inhibiting the translation of the mRNA, or to bind to the GlyT-2 gene to interfere with its transcription. For discussion of the design of nucleotide sequences that bind genomic DNA to interfere with transcription, see Helene, *Anti-Cancer Drug Design* 6, 569, 1991. Once the sequence of the mRNA sought to be bound is known, an antisense molecule can be designed that binds the sense strand by the Watson-Crick base-pairing rules, forming a duplex structure analogous to the DNA double helix. *Gene Regulation: Biology of Antisense RNA and DNA*, Erikson and lxzant, eds., Raven Press, New York, 1991; Helene, *Anti-Cancer Drug Design,* 6:569 (1991); Crooke, *Anti-Cancer Drug Design* 6, 609, 1991.

A serious barrier to fully exploiting this antisense technology is the problem of efficiently introducing into cells a sufficient number of antisense molecules to effectively interfere with the translation of the targeted mRNA or the function of DNA. One method that has been employed to overcome this problem is to covalently modify the 5' or the 3' end of the antisense polynucleic acid molecule with hydrophobic substituents. These modified nucleic acids generally gain access to the cells interior with greater efficiency. See, for example, Boutorin et al., *FEBS Lett.* 23,1382–1390, 1989; Shea et al, *Nucleic Acids Res.* 18, 3777–3783, 1990. Additionally, the phosphate backbone of the antisense molecules has been modified to remove the negative charge for example, Agris et al., Biochemistry 25, 6268, 1986; Cazenave and Helene in *Antisense Nucleic Acids and Proteins: Fundamentals and Applications,* Mol and Van der Krol, eds., p. 47 et seq., Marcel Dekker, New York, 1991) or the purine or pyrimidine bases have been modified (see, for example, *Antisense Nucleic Acids and Proteins: Fundamentals and Applications,* Mol and Van der Krol, eds., p. 47 et seq., Marcel Dekker, New York, 1991; Milligan et al. in *Gene Therapy For Neoplastic Diseases,* Huber and Laso, eds., p. 228 et seq., New York Academy of Sciences, New York, 1994). Other methods to overcome the cell penetration barrier include incorporating the antisense polynucleic acid sequence into an expression vector that can be inserted into the cell in low copy number, but which, when in the cell, can direct the cellular machinery to synthesize more substantial amounts of antisense polynucleic molecules. See, for example, Farhood et al., *Ann. N.Y. Acad. Sci.* 716, 23, 1994. This strategy includes the use of recombinant viruses that have an expression site into which the antisense sequence has been incorporated. See, e.g., Boris-Lawrie and Temin, *Ann. N.Y. Acad. Sci.,* 716:59 (1994). Others have tried to increase membrane permeability by neutralizing the negative charges on antisense molecules or other nucleic acid molecules with polycations. See, e.g. Wu and Wu, *Biochemistry,* 27:887–892, 1988; Behr et al., *Proc. Natl. Acad Sci U.S.A.* 86:6982–6986, 1989.

For gene therapy such as antisense therapy, medical workers often try to incorporate, into one or more cell types of an organism, a DNA vector capable of directing the synthesis of a protein missing from the cell or useful to the cell or organism when expressed in greater amounts. The methods for introducing DNA to cause a cell to produce a new protein or a greater amount of a protein are called "transfection" methods. See, generally, *Neoplastic Diseases,* Huber and Lazo, eds., New York Academy of Science, New York, 1994; Feigner, *Adv. Drug Deli Rev.,* 5:163 (1990); McLachlin, et al., *Progr. Nucl. Acids Res. Mol. Biol.,* 38:91 (1990); Karlsson, S. Blood, 78:2481 (1991); Einerhand and Valerio, *Curr. Top. Microbiol. Immunol,* 177:217–235 (1992); Makdisi et al., Prog. Liver Dis., 10:1 (1992); Litzinger and Huang, *Biochim. Biophys. Acta,* 1113:201 (1992); Morsy et al., *J.A.M.A.,* 270:2338 (1993); Dorudi et al., *British J. Surgery,* 80:566 (1993).

Other general methods of incorporating nucleic acids into cells include calcium phosphate precipitation of nucleic acid and incubation with the target cells (Graham and Van der Eb, *Virology,* 52:456, 1983), co-incubation of nucleic acid, DEAE-dextran and cells (Sompayrac and Danna, *Proc. Natl. Acad. Sci.,* 12:7575, 1981), electroporation of cells in the presence of nucleic acid (Potter et al., *Proc. Natl. Acad. Sci.,* 81:7161–7165, 1984), incorporating nucleic acid into virus coats to create transfection vehicles (Gitman et al., *Proc. Natl. Acad. Sci. U.S.A.,* 82:7309–7313, 1985) and incubating cells with nucleic acid incorporated into liposomes (Wang and Huang, *Proc. Natl. Acad. Sci.,* 84:7851–7855, 1987). One approach to gene therapy is to incorporate the gene sought to be introduced into the cell into a virus, such as a herpes virus, adenovirus, parvovirus or a retrovirus. See, for instance, Akli et al., *Nature Genetics* 3, 224, 1993.

The nucleic acid compositions of the invention can be, for example, administered orally, topically, rectally, nasally, vaginally, by inhalation, for example by use of an aerosol, or parenterally, e.g. iintramuscularly, subcutaneously, intraperitoneally, intraventricularly, or intravenously. The nucleic acid compositions can be administered alone, or they can be combined with a pharmaceutically-acceptable carrier or excipient according to standard pharmaceutical practice. For the oral mode of administration, the nucleic acid compositions can be used in the form of tablets, capsules, lozenges, troches, powders, syrups, elixirs, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added. For parenteral administration, sterile solutions of the conjugate are usually prepared, and the pH of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly (vinyl alcohol), preservatives such as sorbic acid, EDTA or benzylchronium chloride, and the usual quantities of diluents and/or carriers. For pulmonary administration, diluents and/or carriers will be selected to be appropriate to allow the formation of an aerosol.

Generally, the nucleic acid compositions will be administered in an effective amount. For pharmaceutical uses, an effective amount is an amount effective to either (1) reduce the symptoms of the indication sought to be treated or (2) induce a pharmacological change relevant to treating or preventing the indication sought to be treated.

For viral gene therapy vectors, dosages will generally be from about 1 µg to about 1 mg of nucleic acid per kg of body mass. For non-infective gene therapy vectors, dosages will generally be from about 1 µg to about 100 mg of nucleic acid per kg of body mass. Antisense oligonucleotide dosages will generally be from about 1 µg to about 100 mg of nucleic acid per kg of body mass.

Autoimmune Disorders

Autoimmune disorders whereby antibodies are produced against glycine transporters can be expected to be associated with disease states. For example, for the GlyT-2 transporters, such disorders can be expected to be associated with decreased muscle activity, for instance decreased muscle activity that presents much like myasthenia gravis, or to be associated with decreased pain perception. See, for an example of a disease caused by autoantibodies to a molecule involved in neurotransmission (glutamic acid decarboxylase), Nathan et al., *J. Neurosci. Res.* 40: 134–137, 1995.

The presence of these antibodies can be measured by established immunological methods using protein sequences obtained from the nucleic acids described herein or the related glycine transporters reported elsewhere. See, for example, Kim et al., *Mol. Pharmacol.*, 45: 608–617, 1994 and Liu et al., *J. Biol. Chem.* 268: 22802–22808, 1992. Such immunological methods are described, for example, in Ausubel et al., *Short Protocols in Molecular Biology*, John Wiley & Sons, New York, 1992.

The following examples further illustrate the present invention, but of course, should not be construed as in any way limiting its scope.

EXAMPLE 1

GlyT-2 Cloning

The cDNA encoding human GlyT-2 was generated by Reverse-Transcription PCR (RT-PCR) in two steps. In the first step, a degenerate primer corresponding to the rat GlyT-2 nucleotide sequence from 2540 to 2521 (5'-GGRTCDATCATRTTYTTRTA SEQ ID NO:28) was used to prime cDNA synthesis from human spinal cord poly A mRNA (Clontech, Palo Alto, Calif.). The numbering recited herein for the rat sequence is according to the numbering reported in Liu et al., *J. Biol. Chem.* 268: 22802–22808, 1992. The following primer pairs were then used in PCR reactions:

Primer A1: 5'-CCNAARGARATGAAYAARCCNCC (SEQ ID NO:29, based on NT 223–245 of rat sequence)

Primer A2: 5'-GCNGTGAAGTACACCACTTTNCC (SEQ ID NO:30, based on NT 1490–1468 of rat sequence)

Primer B1: 5'-CCNAARGARATGAAYAARCCNCC (SEQ ID NO:29, based on NT 223–245 of rat sequence; same primer as Primer A1)

Primer B2: 5'-GGCYTCNGGGTAARCCACRAANGC (SEQ ID NO:31, based on NT 1872–1849 of rat sequence)

The designation "R" indicates that the oligonucleotide composition has a mixture of adenosine and guanosine at the indicated position; "N" is for mixed oligonucleotides with all four base combinations at the indicated position; "Y" is for mixtures of cytosine and thymidine; "K" is for mixtures of guanosine and thymidine; "D" is for mixtures of adenosine, guanosine and thymidine.

The fragments generated by the A1+A2 primers and by the B1+B2 primers were separately cloned into pCRscript (Stratagene, La Jolla, Calif.) or pCR2.1 (Invitrogen, San Diego, Calif.), and sequenced from the resulting clones using the AutoRead sequencing kit (Pharmacia, Piscataway, N.J.). Comparison of these sequences to rat GlyT-2 using the Lipman-Pearson FASTA algorithm revealed a 89% identity, confirming that these sequences encoded human GlyT-2. The A1+A2 primer pair produced clone phG2-1, which has the nucleic acid sequence of SEQ ID 5 as its insert. The B1+B2 primer pair produced clone phG2-2, which has the nucleic acid sequence of SEQ ID 7 as its insert.

For the second step, cDNA was synthesized from human spinal cord or cerebellum mRNA (Clontech, Palo Alto, Calif.) using random hexamers (Promega, Madison, Wis.), and additional primers were designed based upon the sequence of clones phG2-1 and phG2-2 for PCR. The following primer pairs were used to amplify the 5' and 3' ends of the human GlyT-2 cDNA.

Primer C1: 5'-CGGTTCAATCTGTTGTCCGCATCAGACATG (SEQ ID NO:32, based on NT 181-210 of rat sequence)

Primer C2: 5'-GCAGGCTCGCGCGTCCGCTG (SEQ ID NO:33, based on NT 210-191 of human sequence)

Primer D1: 5'-CCCGTATGTCGTACTCGTGATCCTCCTCATCCG (SEQ ID NO:34, based on NT 1284-1316 of human sequence)

Primer D2: 5'-CCNCCRTGNGTDATCATNGGRAANCCC (SEQ ID NO:35, based on NT 2087-2061 of rat sequence)

Primer E1: 5'-CCCGTATGTCGTACTCGTGATCCTCCTCATCCG (SEQ ID NO:34, based on NT 1284-1316 of human sequence; same primer as Primer D1)

Primer E2: 5'-CCATCCACACTACTGGAYYARCAYTGNGTNCC (SEQ ID NO:36, based on NT 2624-2593 of rat sequence)

Primer F1: 5'-CAGATTTCCTTCTCTTTATCTGCTGCATGG (SEQ ID NO:37, based on NT 1417-1446 of human sequence)

Primer F2: 5'-GGRTCDATCATRTTYTTRTANCKYTCNCC (SEQ ID NO:38, based on NT 2540-2512 of rat sequence)

Primer G1: 5'-CCTGCACCAACAGTGCCACAAGC (SEQ ID NO:39, based on NT 1517-1539 of human sequence)

Primer G2: 5'-CCATCCACACTACTGGAYYARCAYTGNGTNCC (SEQ ID NO:36, based on NT 2624-2593 of rat sequence; same primer as Primer E2)

Primer H1: 5'-CCAAGTACCTACGCACACACAAGCC (SEQ ID NO:40, based on NT 1784-1808 of human sequence)

Primer H2: 5'-GGATTAATACGGGACCATCCACACTACT (SEQ ID NO:41, based on NT 2638-2611 of rat sequence)

The C1+C2 primer pair produced clones phG2-3-a and phGH2-3-b which have the nucleic acid sequences of SEQ IDs 1 and 3 as their inserts, respectively. The D1+D2 primer pair produced phG2-4-a and phGH2-4-b which have the nucleic acid sequences of SEQ IDs 10 and 12 as their inserts, respectively. The E1+E2 primer pair produced a clone which is believed to encompass nucleotides 1317–2379. The F1+F2 primer pair produced a clone which is believed to encompass nucleotides 1447–2298. The G1+G2 primer pair produced clone phG2-7-a, which has the nucleic acid sequence of SEQ ID 14 as its insert and clone phG2-7-b which has the nucleic acid sequence of SEQ ID 16 as its insert. The H1+H2 primer pair produced phG2-8-a and phGH2-8-b which have the nucleic acid sequences of SEQ IDs 22 and 24 as their inserts, respectively.

The PCR fragments were cloned into pCR2.1 (Invitrogen). FIG. 1 shows the location of each of the cloned cDNAs in relation to the entire human GlyT-2 sequence. Clone phG2-3 and phG2-8b were obtained from human cerebellum mRNA while the rest were from spinal cord. The cDNA inserts were sequenced using the AutoRead sequencing kit (Pharmacia) and the ALFexpress™ automatic sequencing apparatus (Pharmacia). These sequences implied ten point variations in the amino acid sequence. The nucleic acid sequence of SEQ ID NO 18 is believed to represent the major consensus sequence. Comparison of the human GlyT-2 DNA sequence of SEQ ID NO 18 to the rat GlyT-2 sequence revealed an 89% nucleic acid identity and a 94.4% amino acid identity using the FASTA algorithm.

EXAMPLE 2

Full-length Clone

Figure 2:
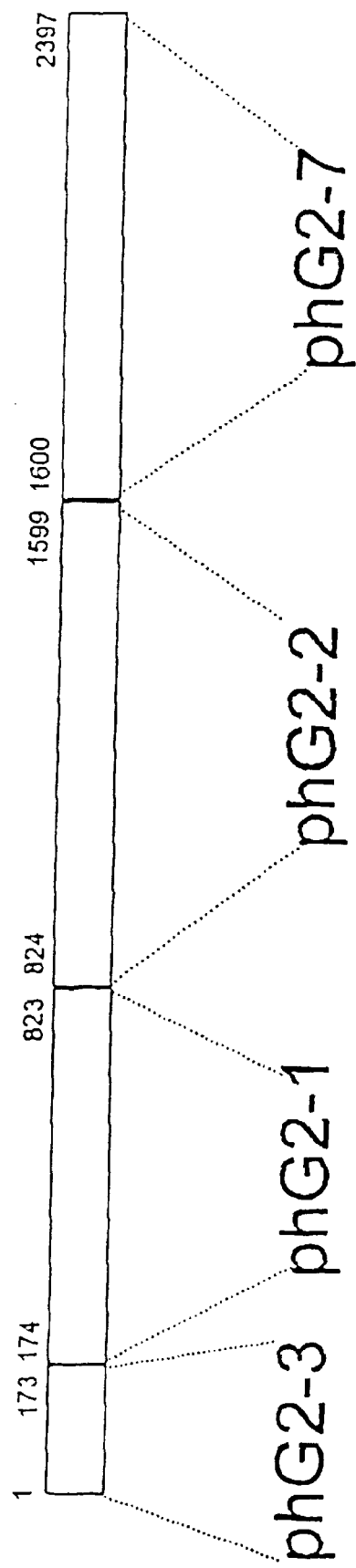
FIG. 2 illustrates which fragment clones were used to construct the clone incorporating the nucleic acid sequence of SEQ ID 20, a full-length clone of the human GlyT-2 gene.

The human GlyT-2 cDNAs were then used to construct a full length human GlyT-2 coding sequence, which was cloned into the pcDNA3 vector (Invitrogen). The clone incorporated the nucleic acid sequence of SEQ ID 20 and was denoted pHGT2. The 5' end of the cDNA was constructed by inserting the 254 bp Hind III-Nar I fragment from clone phG2-3 into clone phG2-1, previously digested with Hind III and Nar I. The 3' end of the cDNA was constructed be inserting the Hind III-Hinc II fragment from phG2-2 and the Hinc II-Xba I fragment from clone phG2-7 into the pcDNA3 vector previously digested with Hind IIII and Xba I. Lastly, the Hind III-Nru I fragment from the 5' end clone and the Nru I-Xba I fragment from the 3' end clone were cloned into the pcDNA3 vector (Invitrogen) digested with Hind IIII and Xba I. The pHGT2 expression clone thus obtained contains the sequence of human GlyT-2 from 1 to 2397 under the control of the human cytomegalovirus (CMV) promoter. In this expression clone, nts 1-173 were derived from clone phG2-3; nts 174-823 were derived from clone phG2-1; nts 824-1599 were derived from clone phG2-2; and nts 1600-2397 were derived from clone phG2-7 (see FIG. 2).

EXAMPLE 3

Second Full-Length Clone

An expression clone containing the nucleic acid sequence of SEQ ID 18 is constructed from the expression clone containing SEQ ID 20 by site-directed mutagenesis to change NT 304 from G to A, NT 371 from T to C, NT 836 from A to T, NT 1116 from G to A, NT 1831 from G to A, NT 2382 from T to C, NT 2388 from A to G, NT 2391 from T to C and NT 2394 from A to G. The mutagenesis is conducted by the oligonucleotide-directed methodology described by Ausubel et al, *Current Protocols in Molecular Biology*, John Wiley and Sons, New York, 1995, pp.8.1.1–8.1.6.

EXAMPLE 4

GlyT-2 Expression

The clone of example 2 was transfected into QT-6 cells (from American Type Culture Collection, Accession No. ATCC CRL-1708) using the method described in Example 5. The glycine transport assay described in Example 6 was used to confirm that glycine transport activity was conferred to the cells by the transfection.

EXAMPLE 5

Transfection

This example sets forth methods and materials used for growing and transfecting QT-6 cells, which are avian fibroblasts derived from quail. Transfections with pHGT2 have been conducted, as have transfections with GlyT-1 vectors, though these latter transfections were conducted at separate times.

QT-6 cells were obtained from American Type Culture Collection (Accession No. ATCC CRL-1708). Complete QT-6 medium for growing QT-6 was Medium 199 (Sigma Chemical Company, St. Louis, Mo.; hereinafter "Sigma") supplemented to be 10% tryptose phosphate; 5% fetal bovine serum (Sigma); 1% penicillin-streptomycin (Sigma); and 1% sterile dimethylsulfoxide (DMSO; Sigma). Other solutions required for growing or transfecting QT-6 cells included:

DNA/DEAE Mix: 450 µl TBS, 450 µl DEAE Dextran (Sigma), and 100 µl of DNA (4 µg) in TE, where the DNA included GlyT-1a, GlyT-1b, GlyT-1c, or GlyT-2 encoding DNA, in a suitable expression vector. The DNA used was as defined below.

PBS: Standard phosphate buffered saline, pH 7.4 including 1 mM $CaCl_2$ and 1 mM $MgCl_2$ sterilized through a 0.2 µm filter.

TBS: One ml of Solution B, 10 ml of Solution A; brought to 100 ml with distilled $H_2O$; filter-sterilized and stored at 4° C.

TE: 0.01M Tris, 0.001M EDTA, pH 8.0.

DEAE dextran: Sigma, #D-9885. A stock solution was prepared consisting of 0.1% (1 mg/ml) of the DEAE dextran in TBS. The stock solution was filter sterilized and frozen in 1 ml aliquots.

Chloroquine: Sigma, #C-6628. A stock solution was prepared consisting of 100 mM chloroquine in $H_2O$. The stock solution was filter-sterilized and stored in 0.5 ml aliquots, frozen.

| Solution A (10X): | |
|---|---|
| NaCl | 8.00 g |
| KCl | 0.38 g |
| $Na_2HPO_4$ | 0.20 g |
| Tris base | 3.00 g |

The solution was adjusted to pH 7.5 with HCl, brought to 100.0 ml with distilled $H_2O$, and filter-sterilized and stored at room temperature.

| Solution B (100X): | |
|---|---|
| $CaCl_2.2H_2O$ | 1.5 g |
| $MgCl_2.6H_2O$ | 1.0 g |

The solution was brought to 100 ml with distilled $H_2O$, and filter-sterilized; the solution was then stored at room temperature.

HBSS: 150 mM NaCl, 20 mM HEPES, 1 mM $CaCl_2$, 10 mM glucose, 5 mM KCl, 1 mM $MgCl_2.H_2O$; adjusted with NaOH to pH 7.4.

Standard growth and passaging procedures used were as follows: Cells were grown in 225 ml flasks. For passaging, cells were washed twice with warm HBSS (5 ml each wash). Two ml of a 0.05% trypsin/EDTA solution was added, the culture was swirled, then the trypsin/EDTA solution was aspirated quickly. The culture was then incubated about 2 minutes (until cells lift off), then 10 ml of QT-6 media was added and the cells are further dislodged by swirling the flask and tapping its bottom. The cells were removed and transferred to a 15 ml conical tube, centrifuged at 1000×g for 10 minutes, and resuspended in 10 ml of QT-6 medium. A sample was removed for counting, the cells were then diluted further to a concentration of $1 \times 10^5$ cells/ml using QT-6 medium, and 65 ml of the culture was added per 225 ml flask of passaged cells.

Transfection was accomplished using cDNAs prepared as follows:

For human GlyT-2 expression, the pHGT2 clone described above was used.

The human GlyT-1a (hGlyT-1a) clone contained the sequence of hGlyT-1a from nucleotide position 183 to 2108 cloned into the pRc/CMV vector (Invitrogen, San Diego, Calif.) as a Hind III-Xba I fragment as described in Kim et al., *Mol. Pharmacol.*, 45: 608–617, 1994. The first 17 nucleotides (corresponding to the first 6 amino acids) of the GlyT-1a sequence reported in this Kim et al. article is actually based on the rat sequence. To determine whether the sequence of human GlyT-1a is different in this region, the 5' region of hGlyT-1a from nucleotide 1 to 212 was obtained by rapid amplification of cDNA ends using the 5' RACE system supplied by Gibco BRL (Gaithersburg, Md.). Sequencing of this 5' region of GlyT-1a confirmed that the first 17 nucleotides of coding sequence are identical in human and rat GlyT-1a.

The human GlyT-1b (hGlyT-1b) clone contained the sequence of hGlyT-1b from nucleotide position 213 to 2274 cloned into the pRc/CMV vector as a Hind IIII-Xba I fragment as described in Kim et al., supra.

The human GlyT-1c (hGlyT-1c) clone contained the sequence of hGlyT-1c from nucleotide position 213 to 2336 cloned into the pRc/CMV vector (Invitrogen) as a Hind IIII-Xba I fragment as described in Kim et al., supra. The Hind IIII-Xba fragment of hGlyT-1c from this clone was subcloned into the pRc/RSV vector. Transfection experiments were performed with GlyT-1c in both the pRc/RSV and pRc/CMV expression vectors.

The following four day procedure for the tranfections was used:

On day 1, QT-6 cells were plated at a density of $1 \times 10^6$ cells in 10 ml of complete QT-6 medium in 100 mm dishes.

On day 2, the medium was aspirated and the cells were washed with 10 ml of PBS followed by 10 ml of TBS. The TBS was aspirated, then 1 ml of the DEAE/DNA mix was added to the plate. The plate was swirled in the hood every 5 minutes. After 30 minutes, 8 ml of 80 $\mu$M chloroquine in QT-6 medium was added and the culture was incubated for 2.5 hours at 37° C. and 5% $CO_2$. The medium was then aspirated and the cells were washed two times with complete QT-6 medium, then 100 ml complete QT-6 medium was added and the cells were returned to the incubator.

On day 3, the cells were removed with trypsin/EDTA as described above, and plated into the wells of 96-well assay plates at approximately $2 \times 10^5$ cells/well.

On day 4, glycine transport was assayed as described in Example 6.

EXAMPLE 6
Glycine Uptake

This example illustrates a method for the measurement of glycine uptake by transfected cultured cells.

Transient GlyT-transfected cells or control cells grown in accordance with Example 5 were washed three times with HEPES buffered saline (HBS). The control cells were treated precisely as the GlyT-transfected cells except that the transfection procedure omitted any cDNA. The cells were incubated 10 minutes at 37° C., after which a solution was added containing 50 nM [$^3$H] glycine (17.5 Ci/mmol) and either (a) no potential competitor, (b) 10 mM nonradioactive glycine or (c) a concentration of a prospective agent. A range of concentrations of the prospective agent was used to generate data for calculating the concentration resulting in 50% of the effect (for example, the $IC_{50}$s, which are the concentrations of agent inhibiting glycine uptake by 50%). The cells were then incubated another 20 minutes at 37° C., after which the cells were washed three times with ice-cold HBS. Scintillant was added to the cells, the cells were shaken for 30 minutes, and the radioactivity in the cells was counted using a scintillation counter. Data were compared between the cells contacted or not contacted by a prospective agent, and, where relevant, between cells having GlyT-1 activity versus cells having GlyT-2 activity, depending on the assay being conducted.

Figure 5:
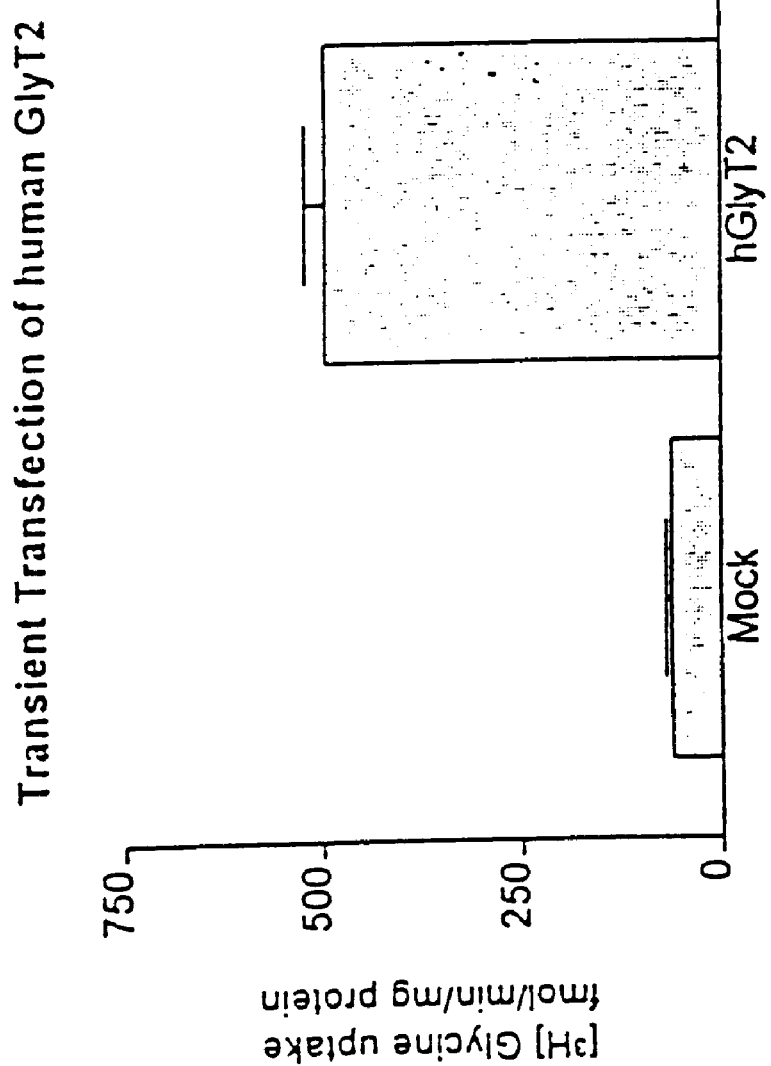
FIG. 5 shows the measurement of glycine transport in QT-6cells either transfected with a human GlyT-2 expression vector or mock transfected.

Expression of glycine transporter activity in QT-6 cells transfected with the human GlyT-2 clone, pHGT2, is demonstrated in FIG. 5, in which [$^3$H] glycine uptake is shown for mock and pHGT2 transfected cells. QT-6 cells transfected with pHGT2 show significant increases in glycine transport as compared to mock transfected control cells. The results are presented as means±SEM of a representative experiment performed in triplicate.

Figure 6:
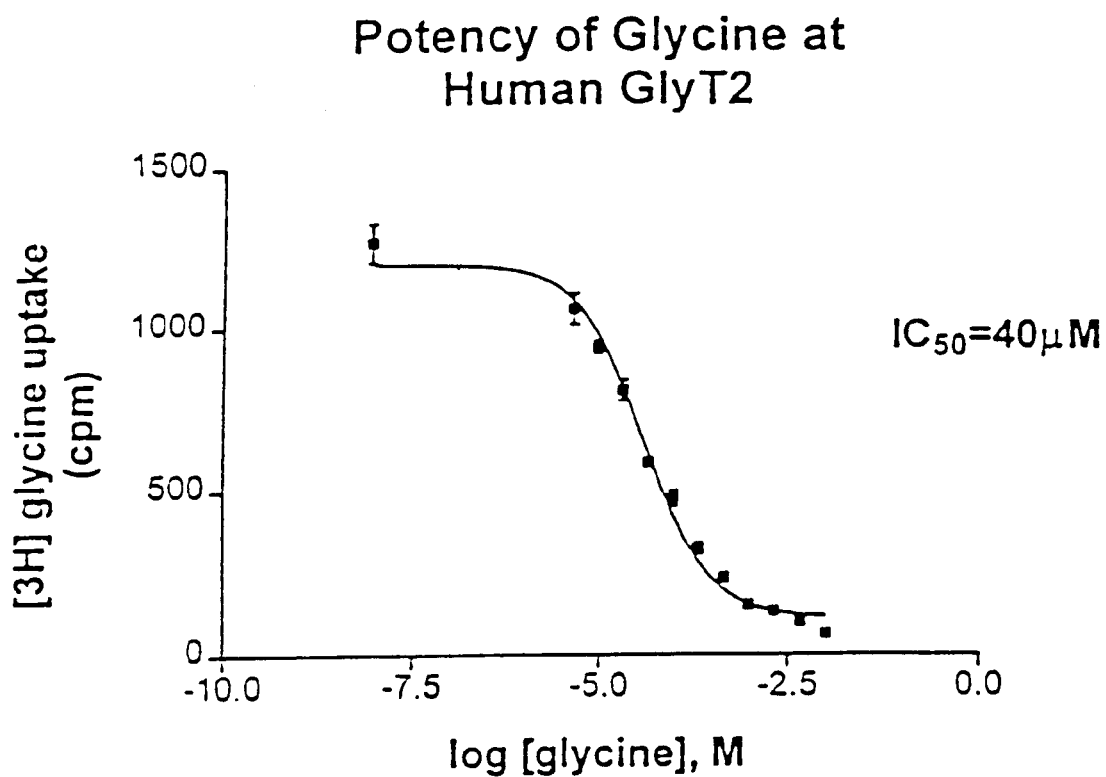
FIG. 6 shows the concentration dependence of glycine transport in QT-6 cells transfected with human GlyT-2.

The concentration dependence of glycine transport in pHGT2-transfected cells is shown in FIG. 6. QT-6 cells transfected with the human GlyT-2 were incubated with 50 nM [$^3$H] glycine and the indicated concentrations of unlabeled glycine for 20 minutes, and the cell-incorporated radioactivity was determined by scintillation counting. Data points represent means±SEM from an experiment performed in quadruplicate. The results indicated an $IC_{50}$ of 40 $\mu$M.

EXAMPLE 7
Calcium Flux

This example illustrates a protocol for measuring calcium flux in cells.

The calcium flux measurement was generally performed in primary cell cultures, which were prepared using standard procedures and techniques that require sterile dissecting equipment, a microscope and defined medium. The protocol used was substantially as described by Lu et al., *Proc. Nat'l. Acad. Sci. USA*, 88: 6289–6292, 1991.

EXAMPLE 8
Binding to Strychnine-Sensitive Receptor

Binding of strychnine to strychnine-sensitive receptors was measured as described in White et al. *J. Neurochem.* 35: 503–512, 1989 and Becker et al., *J. Neurosci.* 6: 1358–1364, 1986, with minor modifications.

---

SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
        (A) LENGTH: 190 base pairs
        (B) TYPE: nucleic acid
        (C) STRANDEDNESS: double
        (D) TOPOLOGY: linear (xi) SEQUENCE DESCRIPTION: SEQ ID NO:1:

```
ATGGATTGCA GTGCTCCCAA GGAAATGAAT AAACTGCCAG CCAACAGCCC GGAGGCGGCG    60

GCGGCGCAGG GCCACCCGGA TGGCCCATGC GCTCCCAGGA CGAGCCCGGA GCAGGAGCTT   120

CCCGCGGCTG CCGCCCCGCC GCCGCCACGT GTGCCCAGGT CCGCTTCCAC CGGCGCCCAA   180

ACTTTCCAGT                                                         190
```

(2) INFORMATION FOR SEQ ID NO:2:

(i) SEQUENCE CHARACTERISTICS:
        (A) LENGTH: 63 amino acids
        (B) TYPE: amino acid
        (C) STRANDEDNESS: single
        (D) TOPOLOGY: linear (xi) SEQUENCE DESCRIPTION: SEQ ID NO:2:

```
Met Asp Cys Ser Ala Pro Lys Glu Met Asn Lys Leu Pro Ala Asn Ser
1               5                  10                  15

Pro Glu Ala Ala Ala Ala Gln Gly His Pro Asp Gly Pro Cys Ala Pro
            20                  25                  30

Arg Thr Ser Pro Glu Gln Glu Leu Pro Ala Ala Ala Pro Pro Pro
        35                  40                  45

Pro Arg Val Pro Arg Ser Ala Ser Thr Gly Ala Gln Thr Phe Gln
    50                  55                  60
```

(2) INFORMATION FOR SEQ ID NO:3:

(i) SEQUENCE CHARACTERISTICS:
        (A) LENGTH: 190 base pairs
        (B) TYPE: nucleic acid
        (C) STRANDEDNESS: double
        (D) TOPOLOGY: linear (xi) SEQUENCE DESCRIPTION: SEQ ID NO:3:

```
ATGGACTGCA GTGCTCCCAA GGAAATGAAT AAACTGCCAG CCAACAGCCC GGAGGCGGCG    60

GCGGCGCAGG GCCACCCGGA TGGCCCATGC GCTCCCAGGA CGAGCCCGGA GCAGGAGCTT   120

CCCGCGGCTG CCGCCCCGCC GCCGCCACGT GTGCCCAGGT CCGCTTCCAC CGGCGCCCAA   180

ACTTTCCAGT                                                         190
```

(2) INFORMATION FOR SEQ ID NO:4:

(i) SEQUENCE CHARACTERISTICS:
        (A) LENGTH: 63 amino acids
        (B) TYPE: amino acid
        (C) STRANDEDNESS: single
        (D) TOPOLOGY: linear (xi) SEQUENCE DESCRIPTION: SEQ ID NO:4:

```
Met Asp Cys Ser Ala Pro Lys Glu Met Asn Lys Leu Pro Ala Asn Ser
1               5                  10                  15

Pro Glu Ala Ala Ala Ala Gln Gly His Pro Asp Gly Pro Cys Ala Pro
            20                  25                  30

Arg Thr Ser Pro Glu Gln Glu Leu Pro Ala Ala Ala Pro Pro Pro
        35                  40                  45

Pro Arg Val Pro Arg Ser Ala Ser Thr Gly Ala Gln Thr Phe Gln
    50                  55                  60
```

(2) INFORMATION FOR SEQ ID NO:5:

(i) SEQUENCE CHARACTERISTICS:
        (A) LENGTH: 1216 base pairs
        (B) TYPE: nucleic acid
        (C) STRANDEDNESS: double (D) TOPOLOGY: linear (xi) SEQUENCE DESCRIPTION: SEQ ID NO:5:

```
AGCCAACAGC CCGGAGGCGG CGGCGGCGCA GGGCCACCCG GATGGCCCAT GCGCTCCCAG      60
GACGAGCCCG GAGCAGGAGC TTCCCGCGGC TGCCGCCCCG CCGCCGCCAC GTGTGCCCAG     120
GTCCGCTTCC ACCGGCGCCC AAACTTTCCA GTCAGCGGAC GCGCGAGCCT GCGAGGCTGA     180
GCGGCCAGGA GTGGGGTCTT GCAAACTCAG TAGCCCGCGG GCGCAGGCGG CCTCTGCAGC     240
TCTGCGGGAC TTGAGAGAGG CGCAAGGCGC GCAGGCCTCG CCCCCTCCCG GGAGCTCCGG     300
GCCCGGCAAC GCGCTGCACT GTAAGATCCC TTTTCTGCGA GGCCCGGAGG GGGATGCGAA     360
CGTGAGTGTG GGCAAGGGCA CCCTGGAGCG GAACAATACC CCTGTTGTGG GCTGGGTGAA     420
CATGAGCCAG AGCACCGTGG TGCTGGGCAC GGATGGAATC ACGTCCGTGC TCCCGGGCAG     480
CGTGGCCACC GTTGCCACCC AGGAGGACGA GCAAGGGGAT GAGAATAAGG CCCGAGGGAA     540
CTGGTCCAGC AAACTGGACT TCATCCTGTC CATGGTGGGG TACGCAGTGG GGCTGGGCAA     600
TGTCTGGAGG TTTCCCTACC TGGCCTTCCA GAACGGGGGA GGTGCTTTCC TCATCCCTTA     660
CCTGATGATG CTGGCTCTGG CTGGATTACC CATCTTCTTC TTGGAGGTGT CGCTGGGCCA     720
GTTTGCCAGC CAGGGACCAG TGTCTGTGTG GAAGGCCATC CCAGCTCTAC AAGGCTGTGG     780
CATCGCGATG CTGATCATCT CTGTCCTAAT AGCCATATAC TACAATGTGA TTATTTGCTA     840
TACACTTTTC TACCTGTTTG CCTCCTTTGT GTCTGTACTA CCCTGGGGCT CCTGCAACAA     900
CCCTTGGAAT ACGCCAGAAT GCAAAGATAA AACCAAACTT TTATTAGATT CCTGTGTTAT     960
CAGTGACCAT CCCAAAATAC AGATCAAGAA CTCGACTTTC TGCATGACCG CTTATCCCAA    1020
CGTGACAATG GTTAATTTCA CCAGCCAGGC CAATAAGACA TTTGTCAGTG GAAGTGAAGA    1080
GTACTTCAAG TACTTTGTGC TGAAGATTTC TGCAGGGATT GAATATCCTG GCGAGATCGG    1140
GTGGCCACTA GCTCTCTGCC TCTTCCTGGC TTGGGTCATT GTGTATGCAT CGTTGGCTAA    1200
AGGAATCAAG ACTTCA                                                    1216
```

(2) INFORMATION FOR SEQ ID NO:6:

(i) SEQUENCE CHARACTERISTICS:
        (A) LENGTH: 405 amino acids
        (B) TYPE: amino acid
        (C) STRANDEDNESS: single
        (D) TOPOLOGY: linear (xi) SEQUENCE DESCRIPTION: SEQ ID NO:6:

```
Ala Asn Ser Pro Glu Ala Ala Ala Gln Gly His Pro Asp Gly Pro
 1               5                  10                  15

Cys Ala Pro Arg Thr Ser Pro Glu Gln Glu Leu Pro Ala Ala Ala
                20                  25                  30

Pro Pro Pro Pro Arg Val Pro Arg Ser Ala Ser Thr Gly Ala Gln Thr
                35                  40                  45

Phe Gln Ser Ala Asp Ala Arg Ala Cys Glu Ala Glu Arg Pro Gly Val
         50                  55                  60

Gly Ser Cys Lys Leu Ser Ser Pro Arg Ala Gln Ala Ala Ser Ala Ala
65                  70                  75                  80

Leu Arg Asp Leu Arg Glu Ala Gln Gly Ala Gln Ala Ser Pro Pro Pro
                85                  90                  95

Gly Ser Ser Gly Pro Gly Asn Ala Leu His Cys Lys Ile Pro Phe Leu
                100                 105                 110

Arg Gly Pro Glu Gly Asp Ala Asn Val Ser Val Gly Lys Gly Thr Leu
                115                 120                 125
```

```
Glu Arg Asn Asn Thr Pro Val Val Gly Trp Val Asn Met Ser Gln Ser
    130                 135                 140

Thr Val Val Leu Gly Thr Asp Gly Ile Thr Ser Val Leu Pro Gly Ser
145                 150                 155                 160

Val Ala Thr Val Ala Thr Gln Glu Asp Glu Gln Gly Asp Glu Asn Lys
                165                 170                 175

Ala Arg Gly Asn Trp Ser Ser Lys Leu Asp Phe Ile Leu Ser Met Val
            180                 185                 190

Gly Tyr Ala Val Gly Leu Gly Asn Val Trp Arg Phe Pro Tyr Leu Ala
        195                 200                 205

Phe Gln Asn Gly Gly Gly Ala Phe Leu Ile Pro Tyr Leu Met Met Leu
    210                 215                 220

Ala Leu Ala Gly Leu Pro Ile Phe Phe Leu Glu Val Ser Leu Gly Gln
225                 230                 235                 240

Phe Ala Ser Gln Gly Pro Val Ser Val Trp Lys Ala Ile Pro Ala Leu
                245                 250                 255

Gln Gly Cys Gly Ile Ala Met Leu Ile Ile Ser Val Leu Ile Ala Ile
            260                 265                 270

Tyr Tyr Asn Val Ile Ile Cys Tyr Thr Leu Phe Tyr Leu Phe Ala Ser
        275                 280                 285

Phe Val Ser Val Leu Pro Trp Gly Ser Cys Asn Asn Pro Trp Asn Thr
    290                 295                 300

Pro Glu Cys Lys Asp Lys Thr Lys Leu Leu Leu Asp Ser Cys Val Ile
305                 310                 315                 320

Ser Asp His Pro Lys Ile Gln Ile Lys Asn Ser Thr Phe Cys Met Thr
                325                 330                 335

Ala Tyr Pro Asn Val Thr Met Val Asn Phe Thr Ser Gln Ala Asn Lys
            340                 345                 350

Thr Phe Val Ser Gly Ser Glu Glu Tyr Phe Lys Tyr Phe Val Leu Lys
        355                 360                 365

Ile Ser Ala Gly Ile Glu Tyr Pro Gly Glu Ile Gly Trp Pro Leu Ala
    370                 375                 380

Leu Cys Leu Phe Leu Ala Trp Val Ile Val Tyr Ala Ser Leu Ala Lys
385                 390                 395                 400

Gly Ile Lys Thr Ser
                405

(2) INFORMATION FOR SEQ ID NO:7:

(i) SEQUENCE CHARACTERISTICS:
        (A) LENGTH: 1597 base pairs
        (B) TYPE: nucleic acid
        (C) STRANDEDNESS: double
        (D) TOPOLOGY: linear (xi) SEQUENCE DESCRIPTION: SEQ ID NO:7:

AGCCAACAGC CCGGAGGCGG CGGCGGCGCA GGGCCACCCG GATGGCCCAT GCGCTCCCAG      60

GACGAGCCCG GAGCAGGAGC TTCCCGCGGC TGCCGCCCCG CCGCCGCCAC GTGTGCCCAG     120

GTCCGCTTCC ACCGGCGCCC AAACTTTCCA GTCAGCGGAC GCGCGAGCCT GCGAGGCTGA     180

GCGGCCAGGA GTGGGGTCTT GCAAACTCAG TAGCCCGCGG GCGCAGGCGG CCTCTGCAGC     240

TCTGCGGGAC TTGAGAGAGG CGCAAAGCGC GCAGGCCTCG CCCCCTCCCG GGAGCTCCGG     300

GCCCGGCAAC GCGCTGCACT GTAAGATCCC TTCTCTGCGA GGCCCGGAGG GGGATGCGAA     360

CGTGAGTGTG GGCAAGGGCA CCCTGGAGCG GAACAATACC CCTGTTGTGG GCTGGGTGAA     420
```

```
CATGAGCCAG AGCACCGTGG TGCTGGGCAC GGATGGAATC ACGTCCGTGC TCCCGGGCAG    480

CGTGGCCACC GTTGCCACCC AGGAGGACGA GCAAGGGGAT GAGAATAAGG CCTGAGGGAA    540

CTGGTCCAGC AAACTGGACT TCATCCTGTC CATGGTGGGG TACGCAGTGG GGCTGGGCAA    600

TGTCTGGAGG TTTCCCTACC TGGCCTTCCA GAACGGGGGA GGTGCTTTCC TCATCCCTTA    660

CCTGATGATG CTGGCTCTGG CTGGATTACC CATCTTCTTC TTGGAGGTGT CGCTGGGCCA    720

GTTTGCCAGC CAGGGACCAG TGTCTGTGTG GAAGGCCATC CCAGCTCTAC AAGGCTGTGG    780

CATCGCGATG CTGATCAACT CTGTCCTAAT AGCCATATAC TACAATGTGA TTATTTGCTA    840

TACACTTTTC TACCTGTTTG CCTCCTTTGT GTCTGTACTA CCCTGGGGCT CCTGCAACAA    900

CCCTTGGAAT ACGCCAGAAT GCAAAGATAA AACCAAACTT TTATTAGATT CCTGTGTTAT    960

CAGTGACCAT CCCAAAATAC AGATCAAGAA CTCGACTTTC TGCATGACCG CTTATCCCAA   1020

CGTGACAATG GTTAATTTCA CCAGCCAGGC CAATAAGACA TTTGTCAGTG GAAGTGAGGA   1080

GTACTTCAAG TACTTTGTGC TGAAGATTTC TGCAGGGATT GAATATCCTG GCGAGATCAG   1140

GTGGCCACTA GCTCTCTGCC TCTTCCTGGC TTGGGTCATT GTGTATGCAT CGTTGGCTAA   1200

AGGAATCAAG ACTTCAGGAA AAGTGGTGTA CTTCACGGCC ACGTTCCCGT ATGTCGTACT   1260

CGTGATCCTC CTCATCCGAG GAGTCACCCT GCCTGGAGCT GGAGCTGGGA TCTGGTACTT   1320

CATCACACCC AAGTGGGAGA AACTCACGGA TGCCACGGTG TGGAAAGATG CTGCCACTCA   1380

GATTTTCTTC TCTTTATCTG CTGCATGGGG AGGCCTGATC ACTCTCTCTT CTTACAACAA   1440

ATTCCACAAC AACTGCTACA GGGACACTCT AATTGTCACC TGCACCAACA GTGCCACAAG   1500

CATCTTTGCC GGCTTCGTCA TCTTCTCCGT TATCGGCTTC ATGGCCAATG AACGCAAAGT   1560

CAACATTGAG AATGTGGCAG ACCAAGGGCC AGGCATT                            1597

(2) INFORMATION FOR SEQ ID NO:8:

(i) SEQUENCE CHARACTERISTICS:
        (A) LENGTH: 177 amino acids
        (B) TYPE: amino acid
        (C) STRANDEDNESS: single
        (D) TOPOLOGY: linear (xi) SEQUENCE DESCRIPTION: SEQ ID NO:8:

Ala Asn Ser Pro Glu Ala Ala Ala Gln Gly His Pro Asp Gly Pro
 1               5                  10                  15

Cys Ala Pro Arg Thr Ser Pro Glu Gln Leu Pro Ala Ala Ala Ala
                20                  25                  30

Pro Pro Pro Arg Val Pro Arg Ser Ala Ser Thr Gly Ala Gln Thr
                35                  40                  45

Phe Gln Ser Ala Asp Ala Arg Ala Cys Glu Ala Glu Arg Pro Gly Val
 50                  55                  60

Gly Ser Cys Lys Leu Ser Ser Pro Arg Ala Gln Ala Ala Ser Ala Ala
65                   70                  75                  80

Leu Arg Asp Leu Arg Glu Ala Gln Ser Ala Gln Ala Ser Pro Pro Pro
                85                  90                  95

Gly Ser Ser Gly Pro Gly Asn Ala Leu His Cys Lys Ile Pro Ser Leu
                100                 105                 110

Arg Gly Pro Glu Gly Asp Ala Asn Val Ser Val Gly Lys Gly Thr Leu
            115                 120                 125

Glu Arg Asn Asn Thr Pro Val Val Gly Trp Val Asn Met Ser Gln Ser
        130                 135                 140

Thr Val Val Leu Gly Thr Asp Gly Ile Thr Ser Val Leu Pro Gly Ser
145                 150                 155                 160
```

Val Ala Thr Val Ala Thr Gln Glu Asp Glu Gln Gly Asp Glu Asn Lys
            165                 170                 175

Ala (2) INFORMATION FOR SEQ ID NO:9:

(i) SEQUENCE CHARACTERISTICS:
       (A) LENGTH: 354 amino acids
       (B) TYPE: amino acid
       (C) STRANDEDNESS: single
       (D) TOPOLOGY: linear (xi) SEQUENCE DESCRIPTION: SEQ ID NO:9:

Gly Asn Trp Ser Ser Lys Leu Asp Phe Ile Leu Ser Met Val Gly Tyr
1               5                   10                  15

Ala Val Gly Leu Gly Asn Val Trp Arg Phe Pro Tyr Leu Ala Phe Gln
                20                  25                  30

Asn Gly Gly Gly Ala Phe Leu Ile Pro Tyr Leu Met Met Leu Ala Leu
            35                  40                  45

Ala Gly Leu Pro Ile Phe Phe Leu Glu Val Ser Leu Gly Gln Phe Ala
        50                  55                  60

Ser Gln Gly Pro Val Ser Val Trp Lys Ala Ile Pro Ala Leu Gln Gly
65                  70                  75                  80

Cys Gly Ile Ala Met Leu Ile Asn Ser Val Leu Ile Ala Ile Tyr Tyr
                85                  90                  95

Asn Val Ile Ile Cys Tyr Thr Leu Phe Tyr Leu Phe Ala Ser Phe Val
                100                 105                 110

Ser Val Leu Pro Trp Gly Ser Cys Asn Asn Pro Trp Asn Thr Pro Glu
            115                 120                 125

Cys Lys Asp Lys Thr Lys Leu Leu Leu Asp Ser Cys Val Ile Ser Asp
        130                 135                 140

His Pro Lys Ile Gln Ile Lys Asn Ser Thr Phe Cys Met Thr Ala Tyr
145                 150                 155                 160

Pro Asn Val Thr Met Val Asn Phe Thr Ser Gln Ala Asn Lys Thr Phe
                165                 170                 175

Val Ser Gly Ser Glu Glu Tyr Phe Lys Tyr Phe Val Leu Lys Ile Ser
            180                 185                 190

Ala Gly Ile Glu Tyr Pro Gly Glu Ile Arg Trp Pro Leu Ala Leu Cys
        195                 200                 205

Leu Phe Leu Ala Trp Val Ile Val Tyr Ala Ser Leu Ala Lys Gly Ile
210                 215                 220

Lys Thr Ser Gly Lys Val Val Tyr Phe Thr Ala Thr Phe Pro Tyr Val
225                 230                 235                 240

Val Leu Val Ile Leu Leu Ile Arg Gly Val Thr Leu Pro Gly Ala Gly
                245                 250                 255

Ala Gly Ile Trp Tyr Phe Ile Thr Pro Lys Trp Glu Lys Leu Thr Asp
            260                 265                 270

Ala Thr Val Trp Lys Asp Ala Ala Thr Gln Ile Phe Phe Ser Leu Ser
        275                 280                 285

Ala Ala Trp Gly Gly Leu Ile Thr Leu Ser Ser Tyr Asn Lys Phe His
        290                 295                 300

Asn Asn Cys Tyr Arg Asp Thr Leu Ile Val Thr Cys Thr Asn Ser Ala
305                 310                 315                 320

Thr Ser Ile Phe Ala Gly Phe Val Ile Phe Ser Val Ile Gly Phe Met
                325                 330                 335

```
      Ala Asn Glu Arg Lys Val Asn Ile Glu Asn Val Ala Asp Gln Gly Pro
                      340                 345                 350

Gly Ile (2) INFORMATION FOR SEQ ID NO:10:

(i) SEQUENCE CHARACTERISTICS:
          (A) LENGTH: 533 base pairs
          (B) TYPE: nucleic acid
          (C) STRANDEDNESS: double
          (D) TOPOLOGY: linear (xi) SEQUENCE DESCRIPTION: SEQ ID NO:10:

AGGAGTCACC CTGCCTGGAG CTGGAGCTGG GATCTGGTAC TTCATCACAC CCAACTGGGA        60

GAAACTCACG GATGCCACGG TGTGGAAAGA TGCTGCCACT CAGATTTTCT TCTCTTTATC       120

TGCTGCATGG GGAGGCCTGA TCACTCTCTC TTCTTACAAC AAATTCCACA ACAACTGCTA       180

CAGGGACACT CTAATTGTCA CCTGCACCAA CAGTGCCACA AGCATCTTTG CCGGCTTCGT       240

CATCTTCTCC GTTATCGGCT TCATGGCCAA TGAACGCAAA GTCAACATTG AGAATGTGGC       300

AGACCAAGGG CCAGGCATTG CATTTGTGGT TTACCCGGAA GCCTTAACCA GGCTGCCTCT       360

CTCTCCGTTC TGGGCCATCA TCTTTTTCCT GATGCTCCTC ACTCTTGGAC TTGACACTAT       420

GTTTGCCACC ATCGAGACCA TAGTGACCTC CATCTCAGAC GAGTTTCCCA AGTACCTACG       480

CACACACAAG CCAGTGTTTA CTCTGGGCTG CTGCATTTGT TTCTTCATCA TGG             533

(2) INFORMATION FOR SEQ ID NO:11:

(i) SEQUENCE CHARACTERISTICS:
          (A) LENGTH: 177 amino acids
          (B) TYPE: amino acid
          (C) STRANDEDNESS: single
          (D) TOPOLOGY: linear (xi) SEQUENCE DESCRIPTION: SEQ ID NO:11:

Gly Val Thr Leu Pro Gly Ala Gly Ala Gly Ile Trp Tyr Phe Ile Thr
  1               5                  10                  15

Pro Asn Trp Glu Lys Leu Thr Asp Ala Thr Val Trp Lys Asp Ala Ala
                 20                  25                  30

Thr Gln Ile Phe Phe Ser Leu Ser Ala Ala Trp Gly Gly Leu Ile Thr
             35                  40                  45

Leu Ser Ser Tyr Asn Lys Phe His Asn Asn Cys Tyr Arg Asp Thr Leu
         50                  55                  60

Ile Val Thr Cys Thr Asn Ser Ala Thr Ser Ile Phe Ala Gly Phe Val
 65                  70                  75                  80

Ile Phe Ser Val Ile Gly Phe Met Ala Asn Glu Arg Lys Val Asn Ile
                 85                  90                  95

Glu Asn Val Ala Asp Gln Gly Pro Gly Ile Ala Phe Val Val Tyr Pro
            100                 105                 110

Glu Ala Leu Thr Arg Leu Pro Leu Ser Pro Phe Trp Ala Ile Ile Phe
            115                 120                 125

Phe Leu Met Leu Leu Thr Leu Gly Leu Asp Thr Met Phe Ala Thr Ile
        130                 135                 140

Glu Thr Ile Val Thr Ser Ile Ser Asp Glu Phe Pro Lys Tyr Leu Arg
145                 150                 155                 160

Thr His Lys Pro Val Phe Thr Leu Gly Cys Cys Ile Cys Phe Phe Ile
                165                 170                 175

Met
```

(2) INFORMATION FOR SEQ ID NO:12:

(i) SEQUENCE CHARACTERISTICS:
        (A) LENGTH: 533 base pairs
        (B) TYPE: nucleic acid
        (C) STRANDEDNESS: double
        (D) TOPOLOGY: linear (xi) SEQUENCE DESCRIPTION: SEQ ID NO:12:

```
AGGAGTCACC CTGCCTGGAG CTGGAGCTGG GATCTGGTAC TTCATCACAC CCAAGTGGGA    60

GAAACTCACG AATGCCACGG TGTGGAAAGA TGCTGCCACT CAGATTTTCT TCTCTTTATC   120

TGCTGCATGG GGAGGCCTGA TCACTCTCTC TTCTTACAAC AAATTCCACA ACAACTGCTA   180

CAGGGACACT CTAATTGTCA CCTGCACCAA CAGTGCCACA AGCATCTTTG CCGGCTTCGT   240

CATCTTCTCC GTTATCGGCT TCATGGCCAA TGAACGCAAA GTCAACATTG AGAATGTGGC   300

AGACCAAGGG CCAGGCATTG CATTTGTGGT TTACCCGGAA GCCTTAACCA GGCTGCCTCT   360

CTCTCCGTTC TGGGCCATCA TCTTTTTCCT GATGCTCCTC ACTCTTGGAC TTGACACTAT   420

GTTTGCCACC ATCGAGACCA TAGTGACCTC CATCTCAGAC GAGTTTCCCA AGTACCTACG   480

CACACACAAG CCAGTGTTTA CTCTGGGCTG CTGCATTTGT TTCTTCATCA TGG          533
```

(2) INFORMATION FOR SEQ ID NO:13:

(i) SEQUENCE CHARACTERISTICS:
        (A) LENGTH: 177 amino acids
        (B) TYPE: amino acid
        (C) STRANDEDNESS: single
        (D) TOPOLOGY: linear (xi) SEQUENCE DESCRIPTION: SEQ ID NO:13:

```
Gly Val Thr Leu Pro Gly Ala Gly Ala Gly Ile Trp Tyr Phe Ile Thr
 1               5                  10                  15

Pro Lys Trp Glu Lys Leu Thr Asn Ala Thr Val Trp Lys Asp Ala Ala
            20                  25                  30

Thr Gln Ile Phe Phe Ser Leu Ser Ala Ala Trp Gly Gly Leu Ile Thr
        35                  40                  45

Leu Ser Ser Tyr Asn Lys Phe His Asn Asn Cys Tyr Arg Asp Thr Leu
    50                  55                  60

Ile Val Thr Cys Thr Asn Ser Ala Thr Ser Ile Phe Ala Gly Phe Val
65                  70                  75                  80

Ile Phe Ser Val Ile Gly Phe Met Ala Asn Glu Arg Lys Val Asn Ile
                85                  90                  95

Glu Asn Val Ala Asp Gln Gly Pro Gly Ile Ala Phe Val Val Tyr Pro
            100                 105                 110

Glu Ala Leu Thr Arg Leu Pro Leu Ser Pro Phe Trp Ala Ile Ile Phe
        115                 120                 125

Phe Leu Met Leu Leu Thr Leu Gly Leu Asp Thr Met Phe Ala Thr Ile
    130                 135                 140

Glu Thr Ile Val Thr Ser Ile Ser Asp Glu Phe Pro Lys Tyr Leu Arg
145                 150                 155                 160

Thr His Lys Pro Val Phe Thr Leu Gly Cys Cys Ile Cys Phe Phe Ile
                165                 170                 175

Met
```

(2) INFORMATION FOR SEQ ID NO:14:

(i) SEQUENCE CHARACTERISTICS:
        (A) LENGTH: 840 base pairs (B) TYPE: nucleic acid
        (C) STRANDEDNESS: double
        (D) TOPOLOGY: linear (xi) SEQUENCE DESCRIPTION: SEQ ID NO:14:

```
ATCTTTGCCG GCTTCGTCAT CTTCTCCGTT ATCGGCTTCA TGGCCAATGA ACGCAAAGTC    60

AACATTGAGA ATGTGGCAGA CCAAGGGCCA GGCATTGCAT TTGTGGTTTA CCCGGAAGCC   120

TTAACCAGGC TGCCTCTCTC TCCGTTCTGG GCCATCATCT TTTTCCTGAT GCTCCTCACT   180

CTTGGACTTG ACACTATGTT TGCCACCATC GAGACCATAG TGACCTCCAT CTCAGACGAG   240

TTTCCCAAGT ACCTACGCAC ACACAAGCCA GTGTTTACTC TGGGCTGCTG CGTTTGTTTC   300

TTCATCATGG GTTTTCCAAT GATCACTCAG GGTGGAATTT ACATGTTTCA GCTTGTGGAC   360

ACCTATGCTG CCTCCTATGC CCTTGTCATC ATTGCCATTT TTGAGCTCGT GGGGATCTCT   420

TATGTGTATG GCTTGCAAAG ATTCTGTGAA GATATAGAGA TGATGATTGG ATTCCAGCCT   480

AACATCTTCT GGAAAGTCTG CTGGGCATTT GTAACCCCAA CCATTTTAAC CTTTATCCTT   540

TGCTTCAGCT TTTACCAGTG GGAGCCCATG ACCTATGCT CTTACCGCTA TCCTAACTGG    600

TCCATGGTGC TCGGATGGCT AATGCTCGCC TGTTCCGTCA TCTGGATCCC AATTATGTTT   660

GTGATAAAAA TGCATCTGGC CCCTGGAAGA TTTATTGAGA GGCTGAAGTT GGTGTGCTCG   720

CCACAGCCGG ACTGGGGCCC ATTCTTAGCT CAACACCGCG GGAGCGTTA CAAGAACATG    780

ATCGACCCCT TGGGAACCTC TTCCTTGGGA CTCAAACTGC CAGTGAAGGA TTTGGAACTG   840
```

(2) INFORMATION FOR SEQ ID NO:15:

(i) SEQUENCE CHARACTERISTICS:
        (A) LENGTH: 280 amino acids
        (B) TYPE: amino acid
        (C) STRANDEDNESS: single
        (D) TOPOLOGY: linear (xi) SEQUENCE DESCRIPTION: SEQ ID NO:15:

```
Ile Phe Ala Gly Phe Val Ile Phe Ser Val Ile Gly Phe Met Ala Asn
  1               5                  10                  15

Glu Arg Lys Val Asn Ile Glu Asn Val Ala Asp Gln Gly Pro Gly Ile
             20                  25                  30

Ala Phe Val Val Tyr Pro Glu Ala Leu Thr Arg Leu Pro Leu Ser Pro
         35                  40                  45

Phe Trp Ala Ile Ile Phe Phe Leu Met Leu Leu Thr Leu Gly Leu Asp
     50                  55                  60

Thr Met Phe Ala Thr Ile Glu Thr Ile Val Thr Ser Ile Ser Asp Glu
 65                  70                  75                  80

Phe Pro Lys Tyr Leu Arg Thr His Lys Pro Val Phe Thr Leu Gly Cys
                 85                  90                  95

Cys Val Cys Phe Phe Ile Met Gly Phe Pro Met Ile Thr Gln Gly Gly
            100                 105                 110

Ile Tyr Met Phe Gln Leu Val Asp Thr Tyr Ala Ala Ser Tyr Ala Leu
        115                 120                 125

Val Ile Ile Ala Ile Phe Glu Leu Val Gly Ile Ser Tyr Val Tyr Gly
    130                 135                 140

Leu Gln Arg Phe Cys Glu Asp Ile Glu Met Met Ile Gly Phe Gln Pro
145                 150                 155                 160

Asn Ile Phe Trp Lys Val Cys Trp Ala Phe Val Thr Pro Thr Ile Leu
                165                 170                 175

Thr Phe Ile Leu Cys Phe Ser Phe Tyr Gln Trp Glu Pro Met Thr Tyr
            180                 185                 190
```

```
Gly Ser Tyr Arg Tyr Pro Asn Trp Ser Met Val Leu Gly Trp Leu Met
            195                 200                 205

Leu Ala Cys Ser Val Ile Trp Ile Pro Ile Met Phe Val Ile Lys Met
            210                 215                 220

His Leu Ala Pro Gly Arg Phe Ile Glu Arg Leu Lys Leu Val Cys Ser
225                 230                 235                 240

Pro Gln Pro Asp Trp Gly Pro Phe Leu Ala Gln His Arg Gly Glu Arg
                245                 250                 255

Tyr Lys Asn Met Ile Asp Pro Leu Gly Thr Ser Ser Leu Gly Leu Lys
            260                 265                 270

Leu Pro Val Lys Asp Leu Glu Leu
            275                 280
```

(2) INFORMATION FOR SEQ ID NO:16:

(i) SEQUENCE CHARACTERISTICS:
        (A) LENGTH: 840 base pairs
        (B) TYPE: nucleic acid
        (C) STRANDEDNESS: double
        (D) TOPOLOGY: linear (xi) SEQUENCE DESCRIPTION: SEQ ID NO:16:

```
ATCTTTGCCG GCTTCGTCAT CTTCTCCGTT ATCGGCTTCA TGGCCAATGA ACGCAAAGTC      60

AACATTGAGA ATGTGGCAGA CCAAGGGCCA GGCATTGCAT TGTGGTTTA CCCGGAAGCC     120

TTAACCAGGC TGCCTCTCTC TCCGTTCTGG GCCATCATCT TTTTCCTGAT GCTCCTCACT    180

CTTGGACTTG ACACTATGTT TGCCACCATC GAGACCATAG TGACCTCCAT CTCAGACGAG    240

TTTCCCAAGT ACCTACGCAC ACACAAGCCA GTGTTTACTC TGGGCTGCTG CATTTGTTTC    300

TTCATCATGG GTTTTCCAAT GATCACTCAG GGTGGAATTT ACATGTTTCA GCTTGTGGAC    360

ACCTATGCTG CCTCCTATGC CCTTGTCATC ATTGCCATTT TTGAGCTCGT GGGGATCTCT    420

TATGTGTATG GCTTGCAAAG ATTCTGTGAA GATATAGAGA TGATGATTGG ATTCCAGCCT    480

AACATCTTCT GGAAAGTCTG CTGGGCATTT GTAACCCCAA CCATTTTAAC CTTTATCCTT    540

TGCTTCAGCT TTTACCAGTG GGAGCCCATG ACCTATGGCT CTTACCGCTA TCCTAACTGG    600

TCCATGGTGC TCGGATGGCT AATGCTCGCC TGTTCCGTCA TCTGGATCCC AATTATGTTT    660

GTGATAAAAA TGCATCTGGC CCCTGGAAGA TTTATTGAGA GGCTGAAGTT GGTGTGCTCG    720

CCACAGCCGG ACTGGGGCCC ATTCTTAGCT CAACACCGCG GGAGCGTTA CAAGAACATG     780

ATCGACCCCT TGGGAACCTC TTCCTTGGGA CTCAAACTGC CAGTGAAGGA TTTGGAACTG    840
```

(2) INFORMATION FOR SEQ ID NO:17:

(i) SEQUENCE CHARACTERISTICS:
        (A) LENGTH: 280 amino acids
        (B) TYPE: amino acid
        (C) STRANDEDNESS: single
        (D) TOPOLOGY: linear (xi) SEQUENCE DESCRIPTION: SEQ ID NO:17:

```
Ile Phe Ala Gly Phe Val Ile Phe Ser Val Ile Gly Phe Met Ala Asn
1               5                   10                  15

Glu Arg Lys Val Asn Ile Glu Asn Val Ala Asp Gln Gly Pro Gly Ile
            20                  25                  30

Ala Phe Val Val Tyr Pro Glu Ala Leu Thr Arg Leu Pro Leu Ser Pro
            35                  40                  45

Phe Trp Ala Ile Ile Phe Phe Leu Met Leu Leu Thr Leu Gly Leu Asp
            50                  55                  60
```

```
Thr Met Phe Ala Thr Ile Glu Thr Ile Val Thr Ser Ile Ser Asp Glu
 65                  70                  75                  80

Phe Pro Lys Tyr Leu Arg Thr His Lys Pro Val Phe Thr Leu Gly Cys
             85                   90                  95

Cys Ile Cys Phe Phe Ile Met Gly Phe Pro Met Ile Thr Gln Gly Gly
            100                 105                 110

Ile Tyr Met Phe Gln Leu Val Asp Thr Tyr Ala Ala Ser Tyr Ala Leu
            115                 120                 125

Val Ile Ile Ala Ile Phe Glu Leu Val Gly Ile Ser Tyr Val Tyr Gly
        130                 135                 140

Leu Gln Arg Phe Cys Glu Asp Ile Glu Met Met Ile Gly Phe Gln Pro
145                 150                 155                 160

Asn Ile Phe Trp Lys Val Cys Trp Ala Phe Val Thr Pro Thr Ile Leu
                165                 170                 175

Thr Phe Ile Leu Cys Phe Ser Phe Tyr Gln Trp Glu Pro Met Thr Tyr
                180                 185                 190

Gly Ser Tyr Arg Tyr Pro Asn Trp Ser Met Val Leu Gly Trp Leu Met
            195                 200                 205

Leu Ala Cys Ser Val Ile Trp Ile Pro Ile Met Phe Val Ile Lys Met
210                 215                 220

His Leu Ala Pro Gly Arg Phe Ile Glu Arg Leu Lys Leu Val Cys Ser
225                 230                 235                 240

Pro Gln Pro Asp Trp Gly Pro Phe Leu Ala Gln His Arg Gly Glu Arg
                245                 250                 255

Tyr Lys Asn Met Ile Asp Pro Leu Gly Thr Ser Ser Leu Gly Leu Lys
                260                 265                 270

Leu Pro Val Lys Asp Leu Glu Leu
            275                 280

(2) INFORMATION FOR SEQ ID NO:18:

(i) SEQUENCE CHARACTERISTICS:
        (A) LENGTH: 2397 base pairs
        (B) TYPE: nucleic acid
        (C) STRANDEDNESS: double
        (D) TOPOLOGY: linear (xi) SEQUENCE DESCRIPTION: SEQ ID NO:18:

ATGGATTGCA GTGCTCCCAA GGAAATGAAT AAACTGCCAG CCAACAGCCC GGAGGCGGCG      60

GCGGCGCAGG GCCACCCGGA TGGCCCATGC GCTCCCAGGA CGAGCCCGGA GCAGGAGCTT     120

CCCGCGGCTG CCGCCCCGCC GCCGCCACGT GTGCCCAGGT CCGCTTCCAC CGGCGCCCAA     180

ACTTTCCAGT CAGCGGACGC GCGAGCCTGC GAGGCTGAGC GGCCAGGAGT GGGGTCTTGC     240

AAACTCAGTA GCCCGCGGGC GCAGGCGGCC TCTGCAGCTC TGCGGGACTT GAGAGAGGCG     300

CAAAGCGCGC AGGCCTCGCC CCCTCCCGGG AGCTCCGGGC CGGCAACGC GCTGCACTGT      360

AAGATCCCTT CTCTGCGAGG CCCGGAGGGG GATGCGAACG TGAGTGTGGG CAAGGGCACC     420

CTGGAGCGGA ACAATACCCC TGTTGTGGGC TGGGTGAACA TGAGCCAGAG CACCGTGGTG     480

CTGGGCACGG ATGGAATCAC GTCCGTGCTC CCGGGCAGCG TGGCCACCGT TGCCACCCAG     540

GAGGACGAGC AAGGGGATGA GAATAAGGCC CGAGGGAACT GGTCCAGCAA ACTGGACTTC     600

ATCCTGTCCA TGGTGGGGTA CGCAGTGGGG CTGGGCAATG TCTGGAGGTT TCCCTACCTG     660

GCCTTCCAGA ACGGGGGAGG TGCTTTCCTC ATCCCTTACC TGATGATGCT GGCTCTGGCT     720

GGATTACCCA TCTTCTTCTT GGAGGTGTCG CTGGGCCAGT TTGCCAGCCA GGGACCAGTG     780
```

```
TCTGTGTGGA AGGCCATCCC AGCTCTACAA GGCTGTGGCA TCGCGATGCT GATCATCTCT    840

GTCCTAATAG CCATATACTA CAATGTGATT ATTTGCTATA CACTTTTCTA CCTGTTTGCC    900

TCCTTTGTGT CTGTACTACC CTGGGGCTCC TGCAACAACC CTTGGAATAC GCCAGAATGC    960

AAAGATAAAA CCAAACTTTT ATTAGATTCC TGTGTTATCA GTGACCATCC CAAAATACAG   1020

ATCAAGAACT CGACTTTCTG CATGACCGCT TATCCCAACG TGACAATGGT TAATTTCACC   1080

AGCCAGGCCA ATAAGACATT TGTCAGTGGA AGTGAAGAGT ACTTCAAGTA CTTTGTGCTG   1140

AAGATTTCTG CAGGGATTGA ATATCCTGGC GAGATCAGGT GGCCACTAGC TCTCTGCCTC   1200

TTCCTGGCTT GGGTCATTGT GTATGCATCG TTGGCTAAAG GAATCAAGAC TTCAGGAAAA   1260

GTGGTGTACT TCACGGCCAC GTTCCCGTAT GTCGTACTCG TGATCCTCCT CATCCGAGGA   1320

GTCACCCTGC CTGGAGCTGG AGCTGGGATC TGGTACTTCA TCACACCCAA GTGGGAGAAA   1380

CTCACGGATG CCACGGTGTG GAAAGATGCT GCCACTCAGA TTTTCTTCTC TTTATCTGCT   1440

GCATGGGGAG GCCTGATCAC TCTCTCTTCT TACAACAAAT TCCACAACAA CTGCTACAGG   1500

GACACTCTAA TTGTCACCTG CACCAACAGT GCCACAAGCA TCTTTGCCGG CTTCGTCATC   1560

TTCTCCGTTA TCGGCTTCAT GGCCAATGAA CGCAAAGTCA ACATTGAGAA TGTGGCAGAC   1620

CAAGGGCCAG GCATTGCATT TGTGGTTTAC CCGGAAGCCT TAACCAGGCT GCCTCTCTCT   1680

CCGTTCTGGG CCATCATCTT TTTCCTGATG CTCCTCACTC TTGGACTTGA CACTATGTTT   1740

GCCACCATCG AGACCATAGT GACCTCCATC TCAGACGAGT TTCCCAAGTA CCTACGCACA   1800

CACAAGCCAG TGTTTACTCT GGGCTGCTGC ATTTGTTTCT TCATCATGGG TTTTCCAATG   1860

ATCACTCAGG GTGGAATTTA CATGTTTCAG CTTGTGGACA CCTATGCTGC CTCCTATGCC   1920

CTTGTCATCA TTGCCATTTT TGAGCTCGTG GGGATCTCTT ATGTGTATGG CTTGCAAAGA   1980

TTCTGTGAAG ATATAGAGAT GATGATTGGA TTCCAGCCTA ACATCTTCTG GAAAGTCTGC   2040

TGGGCATTTG TAACCCCAAC CATTTTAACC TTTATCCTTT GCTTCAGCTT TTACCAGTGG   2100

GAGCCCATGA CCTATGGCTC TTACCGCTAT CCTAACTGGT CCATGGTGCT CGGATGGCTA   2160

ATGCTCGCCT GTTCCGTCAT CTGGATCCCA ATTATGTTTG TGATAAAAAT GCATCTGGCC   2220

CCTGGAAGAT TTATTGAGAG GCTGAAGTTG GTGTGCTCGC ACAGCCGGA CTGGGGCCCA   2280

TTCTTAGCTC AACACCGCGG GGAGCGTTAC AAGAACATGA TCGACCCCTT GGGAACCTCT   2340

TCCTTGGGAC TCAAACTGCC AGTGAAGGAT TTGGAACTGG GCACTCAGTG CTAGTCC      2397
```

(2) INFORMATION FOR SEQ ID NO:19:

(i) SEQUENCE CHARACTERISTICS:
        (A) LENGTH: 797 amino acids
        (B) TYPE: amino acid
        (C) STRANDEDNESS: single
        (D) TOPOLOGY: linear (xi) SEQUENCE DESCRIPTION: SEQ ID NO:19:

```
Met Asp Cys Ser Ala Pro Lys Glu Met Asn Lys Leu Pro Ala Asn Ser
 1               5                  10                  15

Pro Glu Ala Ala Ala Gln Gly His Pro Asp Gly Pro Cys Ala Pro
            20                  25                  30

Arg Thr Ser Pro Glu Gln Glu Leu Pro Ala Ala Ala Pro Pro Pro
        35                  40                  45

Pro Arg Val Pro Arg Ser Ala Ser Thr Gly Ala Gln Thr Phe Gln Ser
50                  55                  60

Ala Asp Ala Arg Ala Cys Glu Ala Glu Arg Pro Gly Val Gly Ser Cys
65                  70                  75                  80
```

-continued

```
Lys Leu Ser Ser Pro Arg Ala Gln Ala Ala Ser Ala Ala Leu Arg Asp
                 85                  90                  95

Leu Arg Glu Ala Gln Ser Ala Gln Ala Ser Pro Pro Gly Ser Ser
            100                 105                 110

Gly Pro Gly Asn Ala Leu His Cys Lys Ile Pro Ser Leu Arg Gly Pro
            115                 120                 125

Glu Gly Asp Ala Asn Val Ser Val Gly Lys Gly Thr Leu Glu Arg Asn
130                 135                 140

Asn Thr Pro Val Val Gly Trp Val Asn Met Ser Gln Ser Thr Val Val
145                 150                 155                 160

Leu Gly Thr Asp Gly Ile Thr Ser Val Leu Pro Gly Ser Val Ala Thr
                165                 170                 175

Val Ala Thr Gln Glu Asp Glu Gln Gly Asp Glu Asn Lys Ala Arg Gly
            180                 185                 190

Asn Trp Ser Ser Lys Leu Asp Phe Ile Leu Ser Met Val Gly Tyr Ala
        195                 200                 205

Val Gly Leu Gly Asn Val Trp Arg Phe Pro Tyr Leu Ala Phe Gln Asn
    210                 215                 220

Gly Gly Gly Ala Phe Leu Ile Pro Tyr Leu Met Met Leu Ala Leu Ala
225                 230                 235                 240

Gly Leu Pro Ile Phe Phe Leu Glu Val Ser Leu Gly Gln Phe Ala Ser
                245                 250                 255

Gln Gly Pro Val Ser Val Trp Lys Ala Ile Pro Ala Leu Gln Gly Cys
            260                 265                 270

Gly Ile Ala Met Leu Ile Ile Ser Val Leu Ile Ala Ile Tyr Tyr Asn
        275                 280                 285

Val Ile Ile Cys Tyr Thr Leu Phe Tyr Leu Phe Ala Ser Phe Val Ser
    290                 295                 300

Val Leu Pro Trp Gly Ser Cys Asn Asn Pro Trp Asn Thr Pro Glu Cys
305                 310                 315                 320

Lys Asp Lys Thr Lys Leu Leu Leu Asp Ser Cys Val Ile Ser Asp His
                325                 330                 335

Pro Lys Ile Gln Ile Lys Asn Ser Thr Phe Cys Met Thr Ala Tyr Pro
            340                 345                 350

Asn Val Thr Met Val Asn Phe Thr Ser Gln Ala Asn Lys Thr Phe Val
        355                 360                 365

Ser Gly Ser Glu Glu Tyr Phe Lys Tyr Phe Val Leu Lys Ile Ser Ala
    370                 375                 380

Gly Ile Glu Tyr Pro Gly Glu Ile Arg Trp Pro Leu Ala Leu Cys Leu
385                 390                 395                 400

Phe Leu Ala Trp Val Ile Val Tyr Ala Ser Leu Ala Lys Gly Ile Lys
                405                 410                 415

Thr Ser Gly Lys Val Val Tyr Phe Thr Ala Thr Phe Pro Tyr Val Val
            420                 425                 430

Leu Val Ile Leu Leu Ile Arg Gly Val Thr Leu Pro Gly Ala Gly Ala
        435                 440                 445

Gly Ile Trp Tyr Phe Ile Thr Pro Lys Trp Glu Lys Leu Thr Asp Ala
    450                 455                 460

Thr Val Trp Lys Asp Ala Ala Thr Gln Ile Phe Phe Ser Leu Ser Ala
465                 470                 475                 480

Ala Trp Gly Gly Leu Ile Thr Leu Ser Ser Tyr Asn Lys Phe His Asn
                485                 490                 495

Asn Cys Tyr Arg Asp Thr Leu Ile Val Thr Cys Thr Asn Ser Ala Thr
            500                 505                 510
```

```
Ser Ile Phe Ala Gly Phe Val Ile Phe Ser Val Ile Gly Phe Met Ala
        515                 520                 525

Asn Glu Arg Lys Val Asn Ile Glu Asn Val Ala Asp Gln Gly Pro Gly
    530                 535                 540

Ile Ala Phe Val Tyr Pro Glu Ala Leu Thr Arg Leu Pro Leu Ser
545                 550                 555                 560

Pro Phe Trp Ala Ile Ile Phe Leu Met Leu Thr Leu Gly Leu
                565                 570                 575

Asp Thr Met Phe Ala Thr Ile Glu Thr Ile Val Thr Ser Ile Ser Asp
                580                 585                 590

Glu Phe Pro Lys Tyr Leu Arg Thr His Lys Pro Val Phe Thr Leu Gly
            595                 600                 605

Cys Cys Ile Cys Phe Phe Ile Met Gly Phe Pro Met Ile Thr Gln Gly
        610                 615                 620

Gly Ile Tyr Met Phe Gln Leu Val Asp Thr Tyr Ala Ala Ser Tyr Ala
625                 630                 635                 640

Leu Val Ile Ile Ala Ile Phe Glu Leu Val Gly Ile Ser Tyr Val Tyr
                645                 650                 655

Gly Leu Gln Arg Phe Cys Glu Asp Ile Glu Met Met Ile Gly Phe Gln
            660                 665                 670

Pro Asn Ile Phe Trp Lys Val Cys Trp Ala Phe Val Thr Pro Thr Ile
            675                 680                 685

Leu Thr Phe Ile Leu Cys Phe Ser Phe Tyr Gln Trp Glu Pro Met Thr
    690                 695                 700

Tyr Gly Ser Tyr Arg Tyr Pro Asn Trp Ser Met Val Leu Gly Trp Leu
705                 710                 715                 720

Met Leu Ala Cys Ser Val Ile Trp Ile Pro Ile Met Phe Val Ile Lys
                725                 730                 735

Met His Leu Ala Pro Gly Arg Phe Ile Glu Arg Leu Lys Leu Val Cys
                740                 745                 750

Ser Pro Gln Pro Asp Trp Gly Pro Phe Leu Ala Gln His Arg Gly Glu
            755                 760                 765

Arg Tyr Lys Asn Met Ile Asp Pro Leu Gly Thr Ser Ser Leu Gly Leu
    770                 775                 780

Lys Leu Pro Val Lys Asp Leu Glu Leu Gly Thr Gln Cys
785                 790                 795

(2) INFORMATION FOR SEQ ID NO:20:

(i) SEQUENCE CHARACTERISTICS:
        (A) LENGTH: 2397 base pairs
        (B) TYPE: nucleic acid
        (C) STRANDEDNESS: double
        (D) TOPOLOGY: linear (xi) SEQUENCE DESCRIPTION: SEQ ID NO:20:

ATGGATTGCA GTGCTCCCAA GGAAATGAAT AAACTGCCAG CCAACAGCCC GGAGGCGGCG      60

GCGGCGCAGG GCCACCCGGA TGGCCCATGC GCTCCCAGGA CGAGCCCGGA GCAGGAGCTT     120

CCCGCGGCTG CCGCCCCGCC GCCGCCACGT GTGCCCAGGT CCGCTTCCAC CGGCGCCCAA     180

ACTTTCCAGT CAGCGGACGC GCGAGCCTGC GAGGCTGAGC GGCCAGGAGT GGGGTCTTGC     240

AAACTCAGTA GCCCGCGGGC GCAGGCGGCC TCTGCAGCTC TGCGGGACTT GAGAGAGGCG     300

CAAGGCGCGC AGGCCTCGCC CCCTCCCGGG AGCTCCGGGC CGGCAACGC GCTGCACTGT      360

AAGATCCCTT TTCTGCGAGG CCCGGAGGGG GATGCGAACG TGAGTGTGGG CAAGGGCACC     420
```

```
CTGGAGCGGA ACAATACCCC TGTTGTGGGC TGGGTGAACA TGAGCCAGAG CACCGTGGTG    480

CTGGGCACGG ATGGAATCAC GTCCGTGCTC CCGGGCAGCG TGGCCACCGT TGCCACCCAG    540

GAGGACGAGC AAGGGGATGA GAATAAGGCC CGAGGGAACT GGTCCAGCAA ACTGGACTTC    600

ATCCTGTCCA TGGTGGGGTA CGCAGTGGGG CTGGGCAATG TCTGGAGGTT TCCCTACCTG    660

GCCTTCCAGA ACGGGGGAGG TGCTTTCCTC ATCCCTTACC TGATGATGCT GGCTCTGGCT    720

GGATTACCCA TCTTCTTCTT GGAGGTGTCG CTGGGCCAGT TTGCCAGCCA GGGACCAGTG    780

TCTGTGTGGA AGGCCATCCC AGCTCTACAA GGCTGTGGCA TCGCGATGCT GATCAACTCT    840

GTCCTAATAG CCATATACTA CAATGTGATT ATTTGCTATA CACTTTTCTA CCTGTTTGCC    900

TCCTTTGTGT CTGTACTACC CTGGGGCTCC TGCAACAACC CTTGGAATAC GCCAGAATGC    960

AAAGATAAAA CCAAACTTTT ATTAGATTCC TGTGTTATCA GTGACCATCC CAAAATACAG   1020

ATCAAGAACT CGACTTTCTG CATGACCGCT TATCCCAACG TGACAATGGT TAATTTCACC   1080

AGCCAGGCCA ATAAGACATT TGTCAGTGGA AGTGAGGAGT ACTTCAAGTA CTTTGTGCTG   1140

AAGATTTCTG CAGGGATTGA ATATCCTGGC GAGATCAGGT GGCCACTAGC TCTCTGCCTC   1200

TTCCTGGCTT GGGTCATTGT GTATGCATCG TTGGCTAAAG GAATCAAGAC TTCAGGAAAA   1260

GTGGTGTACT TCACGGCCAC GTTCCCGTAT GTCGTACTCG TGATCCTCCT CATCCGAGGA   1320

GTCACCCTGC CTGGAGCTGG AGCTGGGATC TGGTACTTCA TCACACCCAA GTGGGAGAAA   1380

CTCACGGATG CCACGGTGTG GAAAGATGCT GCCACTCAGA TTTTCTTCTC TTTATCTGCT   1440

GCATGGGGAG GCCTGATCAC TCTCTCTTCT TACAACAAAT TCCACAACAA CTGCTACAGG   1500

GACACTCTAA TTGTCACCTG CACCAACAGT GCCACAAGCA TCTTTGCCGG CTTCGTCATC   1560

TTCTCCGTTA TCGGCTTCAT GGCCAATGAA CGCAAAGTCA ACATTGAAAA TGTGGCAGAC   1620

CAAGGGCCAG GCATTGCATT TGTGGTTTAC CCGGAAGCCT TAACCAGGCT GCCTCTCTCT   1680

CCGTTCTGGG CCATCATCTT TTTCCTGATG CTCCTCACTC TTGGACTTGA CACTATGTTT   1740

GCCACCATCG AGACCATAGT GACCTCCATC TCAGACGAGT TCCCAAGTA CCTACGCACA   1800

CACAAGCCAG TGTTTACTCT GGGCTGCTGC GTTTGTTTCT TCATCATGGG TTTTCCAATG   1860

ATCACTCAGG GTGGAATTTA CATGTTCAG CTTGTGGACA CCTATGCTGC CTCCTATGCC   1920

CTTGTCATCA TTGCCATTTT TGAGCTCGTG GGGATCTCTT ATGTGTATGC CTTGCAAAGA   1980

TTCTGTGAAG ATATAGAGAT GATGATTGGA TTCCAGCCTA ACATCTTCTG GAAAGTCTGC   2040

TGGGCATTTG TAACCCCAAC CATTTTAACC TTTATCCTTT GCTTCAGCTT TTACCAGTGG   2100

GAGCCCATGA CCTATGGCTC TTACCGCTAT CCTAACTGGT CCATGGTGCT CGGATGGCTA   2160

ATGCTCGCCT GTTCCGTCAT CTGGATCCCA ATTATGTTTG TGATAAAAAT GCATCTGGCC   2220

CCTGGAAGAT TTATTGAGAG GCTGAAGTTG GTGTGCTCGC CACAGCCGGA CTGGGGCCCA   2280

TTCTTAGCTC AACACCGCGG GGAGCGTTAC AAGAACATGA TCGACCCCTT GGGAACCTCT   2340

TCCTTGGGAC TCAAACTGCC AGTGAAGGAT TTGGAACTGG GTACTCAATG TTAATCC     2397
```

(2) INFORMATION FOR SEQ ID NO:21:

(i) SEQUENCE CHARACTERISTICS:
        (A) LENGTH: 797 amino acids
        (B) TYPE: amino acid
        (C) STRANDEDNESS: single
        (D) TOPOLOGY: linear (xi) SEQUENCE DESCRIPTION: SEQ ID NO:21:

```
Met Asp Cys Ser Ala Pro Lys Glu Met Asn Lys Leu Pro Ala Asn Ser
 1               5                  10                  15
```

```
Pro Glu Ala Ala Ala Gln Gly His Pro Asp Gly Pro Cys Ala Pro
         20                  25                  30

Arg Thr Ser Pro Glu Gln Glu Leu Pro Ala Ala Ala Pro Pro
         35                  40                  45

Pro Arg Val Pro Arg Ser Ala Ser Thr Gly Ala Gln Thr Phe Gln Ser
 50                  55                      60

Ala Asp Ala Arg Ala Cys Glu Ala Glu Arg Pro Gly Val Gly Ser Cys
 65                  70                  75                  80

Lys Leu Ser Ser Pro Arg Ala Gln Ala Ala Ser Ala Ala Leu Arg Asp
                 85                  90                  95

Leu Arg Glu Ala Gln Gly Ala Gln Ala Ser Pro Pro Gly Ser Ser
             100                 105                 110

Gly Pro Gly Asn Ala Leu His Cys Lys Ile Pro Phe Leu Arg Gly Pro
         115                 120                 125

Glu Gly Asp Ala Asn Val Ser Val Gly Lys Gly Thr Leu Glu Arg Asn
         130                 135                 140

Asn Thr Pro Val Val Gly Trp Val Asn Met Ser Gln Ser Thr Val Val
145                 150                 155                 160

Leu Gly Thr Asp Gly Ile Thr Ser Val Leu Pro Gly Ser Val Ala Thr
             165                 170                 175

Val Ala Thr Gln Glu Asp Glu Gln Gly Asp Glu Asn Lys Ala Arg Gly
             180                 185                 190

Asn Trp Ser Ser Lys Leu Asp Phe Ile Leu Ser Met Val Gly Tyr Ala
         195                 200                 205

Val Gly Leu Gly Asn Val Trp Arg Phe Pro Tyr Leu Ala Phe Gln Asn
         210                 215                 220

Gly Gly Gly Ala Phe Leu Ile Pro Tyr Leu Met Met Leu Ala Leu Ala
225                 230                 235                 240

Gly Leu Pro Ile Phe Phe Leu Glu Val Ser Leu Gly Gln Phe Ala Ser
             245                 250                 255

Gln Gly Pro Val Ser Val Trp Lys Ala Ile Pro Ala Leu Gln Gly Cys
             260                 265                 270

Gly Ile Ala Met Leu Ile Asn Ser Val Leu Ile Ala Ile Tyr Tyr Asn
         275                 280                 285

Val Ile Ile Cys Tyr Thr Leu Phe Tyr Leu Phe Ala Ser Phe Val Ser
         290                 295                 300

Val Leu Pro Trp Gly Ser Cys Asn Asn Pro Trp Asn Thr Pro Glu Cys
305                 310                 315                 320

Lys Asp Lys Thr Lys Leu Leu Leu Asp Ser Cys Val Ile Ser Asp His
             325                 330                 335

Pro Lys Ile Gln Ile Lys Asn Ser Thr Phe Cys Met Thr Ala Tyr Pro
             340                 345                 350

Asn Val Thr Met Val Asn Phe Thr Ser Gln Ala Asn Lys Thr Phe Val
         355                 360                 365

Ser Gly Ser Glu Glu Tyr Phe Lys Tyr Phe Val Leu Lys Ile Ser Ala
         370                 375                 380

Gly Ile Glu Tyr Pro Gly Glu Ile Arg Trp Pro Leu Ala Leu Cys Leu
385                 390                 395                 400

Phe Leu Ala Trp Val Ile Val Tyr Ala Ser Leu Ala Lys Gly Ile Lys
             405                 410                 415

Thr Ser Gly Lys Val Val Tyr Phe Thr Ala Thr Phe Pro Tyr Val Val
             420                 425                 430

Leu Val Ile Leu Leu Ile Arg Gly Val Thr Leu Pro Gly Ala Gly Ala
             435                 440                 445
```

Gly Ile Trp Tyr Phe Ile Thr Pro Lys Trp Glu Lys Leu Thr Asp Ala
    450                 455                 460

Thr Val Trp Lys Asp Ala Ala Thr Gln Ile Phe Phe Ser Leu Ser Ala
465                 470                 475                 480

Ala Trp Gly Gly Leu Ile Thr Leu Ser Ser Tyr Asn Lys Phe His Asn
                485                 490                 495

Asn Cys Tyr Arg Asp Thr Leu Ile Val Thr Cys Thr Asn Ser Ala Thr
            500                 505                 510

Ser Ile Phe Ala Gly Phe Val Ile Phe Ser Val Ile Gly Phe Met Ala
        515                 520                 525

Asn Glu Arg Lys Val Asn Ile Glu Asn Val Ala Asp Gln Gly Pro Gly
    530                 535                 540

Ile Ala Phe Val Val Tyr Pro Glu Ala Leu Thr Arg Leu Pro Leu Ser
545                 550                 555                 560

Pro Phe Trp Ala Ile Ile Phe Phe Leu Met Leu Leu Thr Leu Gly Leu
                565                 570                 575

Asp Thr Met Phe Ala Thr Ile Glu Thr Ile Val Thr Ser Ile Ser Asp
            580                 585                 590

Glu Phe Pro Lys Tyr Leu Arg Thr His Lys Pro Val Phe Thr Leu Gly
        595                 600                 605

Cys Cys Val Cys Phe Phe Ile Met Gly Phe Pro Met Ile Thr Gln Gly
    610                 615                 620

Gly Ile Tyr Met Phe Gln Leu Val Asp Thr Tyr Ala Ala Ser Tyr Ala
625                 630                 635                 640

Leu Val Ile Ile Ala Ile Phe Glu Leu Val Gly Ile Ser Tyr Val Tyr
                645                 650                 655

Gly Leu Gln Arg Phe Cys Glu Asp Ile Glu Met Met Ile Gly Phe Gln
            660                 665                 670

Pro Asn Ile Phe Trp Lys Val Cys Trp Ala Phe Val Thr Pro Thr Ile
        675                 680                 685

Leu Thr Phe Ile Leu Cys Phe Ser Phe Tyr Gln Trp Glu Pro Met Thr
    690                 695                 700

Tyr Gly Ser Tyr Arg Tyr Pro Asn Trp Ser Met Val Leu Gly Trp Leu
705                 710                 715                 720

Met Leu Ala Cys Ser Val Ile Trp Ile Pro Ile Met Phe Val Ile Lys
                725                 730                 735

Met His Leu Ala Pro Gly Arg Phe Ile Glu Arg Leu Lys Leu Val Cys
            740                 745                 750

Ser Pro Gln Pro Asp Trp Gly Pro Phe Leu Ala Gln His Arg Gly Glu
        755                 760                 765

Arg Tyr Lys Asn Met Ile Asp Pro Leu Gly Thr Ser Ser Leu Gly Leu
    770                 775                 780

Lys Leu Pro Val Lys Asp Leu Glu Leu Gly Thr Gln Cys
785                 790                 795

(2) INFORMATION FOR SEQ ID NO:22:

(i) SEQUENCE CHARACTERISTICS:
        (A) LENGTH: 589 base pairs
        (B) TYPE: nucleic acid
        (C) STRANDEDNESS: double
        (D) TOPOLOGY: linear (xi) SEQUENCE DESCRIPTION: SEQ ID NO:22:

AGTGTTTACT CTGGGCTGCT ACATTTGTTT CTTCATCATG GGTTTTCCAA TGATCACTCA    60

```
GGGTGGAATT TACATGTTTC AGCTTGTGGA CACCTATGCT GCCTCCTATG CCCTTGTCAT      120

CATTGCCATT TTTGAGCTCG TGGGGATCTC TTATGTGTAT GGCTTGCAAA GATTCTGTGA      180

AGATATAGAG ATGATGATTG GATTCCAGCC TAACATCTTC TGGAAAGTCT GCTGGGCATT      240

TGTAACCCCA ACCATTTTAA CCTTTATCCT TTGCTTCAGC TTTTACCAGT GGGAGCCCAT      300

GACCTATGGC TCTTACCGCT ATCCTAACTG GTCCATGGTG CTCGGATGGC TAATGCTCGC      360

CTGTTCCGTC ATCTGGATCC CAATTATGTT TGTGGTAAAA ATGCATCTGG CCCCTGGAAG      420

ATTTATTGAG AGGCTGAAGT TGGTGTGCTC GCCACAGCCG GACTGGGGCC CATTCTTAGC      480

TCAACACCGC GGGGAGCGTT ACAAGAACAT GATCGACCCC TTGGGAACCT CTTCCTTGGG      540

ACTCAAACTG CCAGTGAAGG ATTTGGAACT GGGCACTCAG TGCTAGTCC                  589
```

(2) INFORMATION FOR SEQ ID NO:23:

(i) SEQUENCE CHARACTERISTICS:
        (A) LENGTH: 194 amino acids
        (B) TYPE: amino acid
        (C) STRANDEDNESS: single
        (D) TOPOLOGY: linear (xi) SEQUENCE DESCRIPTION: SEQ ID NO:23:

```
Val Phe Thr Leu Gly Cys Tyr Ile Cys Phe Phe Ile Met Gly Phe Pro
 1               5                  10                  15

Met Ile Thr Gln Gly Gly Ile Tyr Met Phe Gln Leu Val Asp Thr Tyr
            20                  25                  30

Ala Ala Ser Tyr Ala Leu Val Ile Ile Ala Ile Phe Glu Leu Val Gly
        35                  40                  45

Ile Ser Tyr Val Tyr Gly Leu Gln Arg Phe Cys Glu Asp Ile Glu Met
    50                  55                  60

Met Ile Gly Phe Gln Pro Asn Ile Phe Trp Lys Val Cys Trp Ala Phe
65                  70                  75                  80

Val Thr Pro Thr Ile Leu Thr Phe Ile Leu Cys Phe Ser Phe Tyr Gln
                85                  90                  95

Trp Glu Pro Met Thr Tyr Gly Ser Tyr Arg Tyr Pro Asn Trp Ser Met
            100                 105                 110

Val Leu Gly Trp Leu Met Leu Ala Cys Ser Val Ile Trp Ile Pro Ile
        115                 120                 125

Met Phe Val Val Lys Met His Leu Ala Pro Gly Arg Phe Ile Glu Arg
    130                 135                 140

Leu Lys Leu Val Cys Ser Pro Gln Pro Asp Trp Gly Pro Phe Leu Ala
145                 150                 155                 160

Gln His Arg Gly Glu Arg Tyr Lys Asn Met Ile Asp Pro Leu Gly Thr
                165                 170                 175

Ser Ser Leu Gly Leu Lys Leu Pro Val Lys Asp Leu Glu Leu Gly Thr
            180                 185                 190

Gln Cys
```

(2) INFORMATION FOR SEQ ID NO:24:

(i) SEQUENCE CHARACTERISTICS:
        (A) LENGTH: 589 base pairs
        (B) TYPE: nucleic acid
        (C) STRANDEDNESS: double
        (D) TOPOLOGY: linear (xi) SEQUENCE DESCRIPTION: SEQ ID NO:24:

```
AGTGTTTACT CTGGGCTGCT GCATTTGTTT CTTCATCATG GGTTTTCCAA TGATCACTCA       60
```

```
GGGTGGAATT TACATGTTTC AGCTTGTGGA CACCTATGCT GCCTCCTATG CCCTTGTCAT    120

CATTGCCATT TTTGAGCTCG TGGGGATCTC TTATGTGTAT GGCTTGCAAA GATTCTGTGA    180

AGATATAGAG ATGATGATTG GATTCCAGCC TAACATCTTC TGGAAAGTCT GCTGGGCATT    240

TGTAACCCCA ACCATTTTAA CCTTTATCCT TTGCTTCAGC TTTTACCAGT GGGAACCCAT    300

GACCTATGGC TCTTACCGCT ATCCTAACTG GTCCATGGTG CTCGGATGGC TAATGCTCGC    360

CTGTTCCGTC ATCTGGATCC CAATTATGTC TGTGATAAAA ATGCATCTGG CCCCTGGAAG    420

ATTTATTGAG AGGCTGAAGT TGGTGTGCTC GCCACAGCCG GACTGGGGCC CATTCTTAGC    480

TCAACACCGC GGGGAGCGTT ACAAGAACAT GATCGACCCC TTGGGAACCT CTTCCTTGGG    540

ACTCAAACTG CCAGTGAAGG ATTTGGAACT GGGCACTCAG TGCTAGTCC               589
```

(2) INFORMATION FOR SEQ ID NO:25:

(i) SEQUENCE CHARACTERISTICS:
        (A) LENGTH: 194 amino acids
        (B) TYPE: amino acid
        (C) STRANDEDNESS: single
        (D) TOPOLOGY: linear (xi) SEQUENCE DESCRIPTION: SEQ ID NO:25:

```
Val Phe Thr Leu Gly Cys Cys Ile Cys Phe Phe Ile Met Gly Phe Pro
 1               5                  10                  15

Met Ile Thr Gln Gly Gly Ile Tyr Met Phe Gln Leu Val Asp Thr Tyr
            20                  25                  30

Ala Ala Ser Tyr Ala Leu Val Ile Ile Ala Ile Phe Glu Leu Val Gly
        35                  40                  45

Ile Ser Tyr Val Tyr Gly Leu Gln Arg Phe Cys Glu Asp Ile Glu Met
    50                  55                  60

Met Ile Gly Phe Gln Pro Asn Ile Phe Trp Lys Val Cys Trp Ala Phe
65                  70                  75                  80

Val Thr Pro Thr Ile Leu Thr Phe Ile Leu Cys Phe Ser Phe Tyr Gln
                85                  90                  95

Trp Glu Pro Met Thr Tyr Gly Ser Tyr Arg Tyr Pro Asn Trp Ser Met
            100                 105                 110

Val Leu Gly Trp Leu Met Leu Ala Cys Ser Val Ile Trp Ile Pro Ile
        115                 120                 125

Met Ser Val Ile Lys Met His Leu Ala Pro Gly Arg Phe Ile Glu Arg
    130                 135                 140

Leu Lys Leu Val Cys Ser Pro Gln Pro Asp Trp Gly Pro Phe Leu Ala
145                 150                 155                 160

Gln His Arg Gly Glu Arg Tyr Lys Asn Met Ile Asp Pro Leu Gly Thr
                165                 170                 175

Ser Ser Leu Gly Leu Lys Leu Pro Val Lys Asp Leu Glu Leu Gly Thr
            180                 185                 190

Gln Cys
```

(2) INFORMATION FOR SEQ ID NO:26:

(i) SEQUENCE CHARACTERISTICS:
        (A) LENGTH: 2403 base pairs
        (B) TYPE: nucleic acid
        (C) STRANDEDNESS: double
        (D) TOPOLOGY: linear (xi) SEQUENCE DESCRIPTION: SEQ ID NO:26:

```
ATGGATTGCA GTGCTCCCAA GGAAATGAAT AAACCACCAA CCAACATCTT GGAGGCAACG    60
```

-continued

```
GTGCCGGGCC ACCGGGATAG CCCTCGAGCA CCTAGGACCA GCCCTGAGCA GGATCTTCCT    120
GCGGCAGCCC CCGCGGCCGC TGTCCAGCCG CCACGTGTGC CCAGGTCGGC TTCCACCGGC    180
GCCCAAACTT TCCAGTCTGC GGATGCGAGA GCCTGTGAGG CACAGCGGCC TGGAGTAGGG    240
TTTTGTAAAC TTAGCAGCCC CCAGGCACAA GCGACCTCTG CGGCCCTCCG GGACTTAAGC    300
GAAGGGCACA GCGCACAGGC CAATCCCCCT TCCGGGGCCG CTGGGGCTGG CAACGCTTTA    360
CACTGCAAGA TTCCAGCTCT GCGTGGCCCG GAGGAGGACG AGAACGTGAG TGTGGCCAAG    420
GGCACGCTGG AGCACAACAA TACCCCACCC GTGGGCTGGG TGAATATGAG CCAGAGCACA    480
GTGGTGTTGG GTACCGATGG AATCGCGTCG GTGCTCCCGG GCAGCGTGGC CACCACTACC    540
ATTCCGGAGG ACGAGCAAGG GGATGAGAAT AAGGCCAGAG GGAACTGGTC CAGCAAACTG    600
GACTTCATCC TGTCCATGGT GGGGTACGCA GTGGGCTGG GTAATGTTTG GAGGTTTCCC    660
TACCTGGCCT TCCAGAACGG GGGAGGTGCT TTCCTCATCC CTTACTTGAT GATGCTGGCA    720
CTGGCTGGCT TACCTATCTT CTTCCTAGAG GTGTCCCTGG GCCAGTTTGC CAGCCAGGGT    780
CCTGTGTCTG TGTGGAAGGC CATCCCAGCT CTGCAGGGCT GTGGCATTGC GATGCTCATC    840
ATCTCCGTCC TCATAGCCAT CTACTACAAC GTCATCATCT GCTACACGCT CTTCTACCTG    900
TTTGCTTCTT TTGTGTCTGT GCTGCCCTGG GGATCCTGCA ACAACCCGTG GAACACACCA    960
GAATGCAAAG ACAAAACCAA ACTTTTACTA GATTCCTGTG TTATCGGTGA CCATCCCAAG   1020
ATACAGATCA AGAACTCTAC TTTCTGCATG ACTGCCTATC CGAACTTGAC CATGGTTAAC   1080
TTCACCAGCC AGGCCAATAA GACATTTGTC AGCGGGAGTG AAGAGTACTT CAAGTACTTT   1140
GTGCTGAAGA TTTCTGCAGG GATTGAATAT CCTGGTGAGA TCAGGTGGCC CTTGCCGTTC   1200
TGCCTTTTCC TGGCCTGGGT GATTGTATAT GCATCGCTGG CAAAAGGAAT TAAGACATCA   1260
GGAAAAGTGG TGTACTTCAC AGCCACCTTC CCTTATGTCG TCCTGGTCAT CCTCCTCATT   1320
CGAGGGGTCA CCCTGCCTGG AGCTGGAGCC GGTATCTGGT ACTTCATCAC ACCTAAGTGG   1380
GAGAAACTCA CGGATGCCAC GGTGTGGAAG GATGCAGCCA CTCAGATTTT CTTCTCCCTG   1440
TCTGCGGCCT GGGGAGGGCT CATCACTCTT TCTTCTTACA ACAAATTCCA TAACAACTGC   1500
TACAGGGACA CGTTAATTGT AACCTGCACC AACAGTGCCA CTAGCATCTT CGCTGGGTTT   1560
GTCATCTTCT CTGTCATTGG CTTCATGGCC AACGAGCGCA AAGTCAACAT TGAGAATGTG   1620
GCTGACCAAG GGCCAGGCAT TGCATTTGTG GTTTACCCAG AAGCCTTAAC CAGGCTGCCT   1680
CTCTCTCCAT TCTGGGCCAT CATCTTTTTC CTGATGCTTC TCACGCTTGG ACTTGACACC   1740
ATGTTTGCTA CCATCGAGAC CATTGTGACC TCCATCTCGG ATGAGTTTCC CAAGTATCTG   1800
CGCACACACA AGCCTGTGTT CACCCTGGGC TGCTGCATCT GCTTCTTCAT TATGGGCTTC   1860
CCAATGATCA CACAGGGTGG AATCTACATG TTTCAGCTTG TGGACACCTA TGCTGCCTCC   1920
TATGCTCTTG TCATCATTGC CATATTTGAG CTTGTTGGCA TCTCCTATGT GTACGGCTTG   1980
CAGAGGTTCT GTGAAGACAT CGAGATGATG ATTGGATTCC AGCCCAACAT TTTCTGGAAG   2040
GTCTGCTGGG CGTTTGTCAC ACCGACCATT TTAACGTTTA TCCTTTGCTT CAGCTTCTAT   2100
CAGTGGGAGC CCATGACCTA TGGCTCCTAC CGCTACCCTA ACTGGTCCAT GGTGCTTGGA   2160
TGGCTGATGC TCGCCTGCTC CGTGATCTGG ATCCCGATTA TGTTCGTGAT AAAAATGTAT   2220
CTGGCTCCTG GGAGATTTAT TGAGAGGCTG AAGTTGGTAT GCTCGCCACA GCCGGACTGG   2280
GGCCCATTCT TAGCTCAGCA CCGCGGGGAA CGCTACAAGA ATATGATCGA CCCCTTGGGA   2340
ACCTCGTCCC TGGGACTCAA GCTGCCAGTG AAGGATTTGG AACTGGGCAC CCAGTGCTAG   2400
TCC                                                                 2403
```

(2) INFORMATION FOR SEQ ID NO:27:

(i) SEQUENCE CHARACTERISTICS:
        (A) LENGTH: 799 amino acids
        (B) TYPE: amino acid
        (C) STRANDEDNESS: single
        (D) TOPOLOGY: linear (xi) SEQUENCE DESCRIPTION: SEQ ID NO:27:

```
Met Asp Cys Ser Ala Pro Lys Glu Met Asn Lys Pro Pro Thr Asn Ile
 1               5                  10                  15

Leu Glu Ala Thr Val Pro Gly His Arg Asp Ser Pro Arg Ala Pro Arg
             20                  25                  30

Thr Ser Pro Glu Gln Asp Leu Pro Ala Ala Pro Ala Ala Ala Val
         35                  40                  45

Gln Pro Pro Arg Val Pro Arg Ser Ala Ser Thr Gly Ala Gln Thr Phe
     50                  55                  60

Gln Ser Ala Asp Ala Arg Ala Cys Glu Ala Gln Arg Pro Gly Val Gly
 65                  70                  75                  80

Phe Cys Lys Leu Ser Ser Pro Gln Ala Gln Ala Thr Ser Ala Ala Leu
                 85                  90                  95

Arg Asp Leu Ser Glu Gly His Ser Ala Gln Ala Asn Pro Pro Ser Gly
            100                 105                 110

Ala Ala Gly Ala Gly Asn Ala Leu His Cys Lys Ile Pro Ala Leu Arg
        115                 120                 125

Gly Pro Glu Glu Asp Glu Asn Val Ser Val Ala Lys Gly Thr Leu Glu
    130                 135                 140

His Asn Asn Thr Pro Pro Val Gly Trp Val Asn Met Ser Gln Ser Thr
145                 150                 155                 160

Val Val Leu Gly Thr Asp Gly Ile Ala Ser Val Leu Pro Gly Ser Val
                165                 170                 175

Ala Thr Thr Thr Ile Pro Glu Asp Glu Gln Gly Asp Glu Asn Lys Ala
            180                 185                 190

Arg Gly Asn Trp Ser Ser Lys Leu Asp Phe Ile Leu Ser Met Val Gly
        195                 200                 205

Tyr Ala Val Gly Leu Gly Asn Val Trp Arg Phe Pro Tyr Leu Ala Phe
    210                 215                 220

Gln Asn Gly Gly Gly Ala Phe Leu Ile Pro Tyr Leu Met Met Leu Ala
225                 230                 235                 240

Leu Ala Gly Leu Pro Ile Phe Phe Leu Glu Val Ser Leu Gly Gln Phe
                245                 250                 255

Ala Ser Gln Gly Pro Val Ser Val Trp Lys Ala Ile Pro Ala Leu Gln
            260                 265                 270

Gly Cys Gly Ile Ala Met Leu Ile Ile Ser Val Leu Ile Ala Ile Tyr
        275                 280                 285

Tyr Asn Val Ile Cys Tyr Thr Leu Phe Tyr Leu Phe Ala Ser Phe
    290                 295                 300

Val Ser Val Leu Pro Trp Gly Ser Cys Asn Asn Pro Trp Asn Thr Pro
305                 310                 315                 320

Glu Cys Lys Asp Lys Thr Lys Leu Leu Leu Asp Ser Cys Val Ile Gly
                325                 330                 335

Asp His Pro Lys Ile Gln Ile Lys Asn Ser Thr Phe Cys Met Thr Ala
            340                 345                 350

Tyr Pro Asn Leu Thr Met Val Asn Phe Thr Ser Gln Ala Asn Lys Thr
        355                 360                 365
```

```
Phe Val Ser Gly Ser Glu Glu Tyr Phe Lys Tyr Phe Val Leu Lys Ile
370                 375                 380

Ser Ala Gly Ile Glu Tyr Pro Gly Glu Ile Arg Trp Pro Leu Pro Phe
385                 390                 395                 400

Cys Leu Phe Leu Ala Trp Val Ile Val Tyr Ala Ser Leu Ala Lys Gly
                405                 410                 415

Ile Lys Thr Ser Gly Lys Val Val Tyr Phe Thr Ala Thr Phe Pro Tyr
            420                 425                 430

Val Val Leu Val Ile Leu Leu Ile Arg Gly Val Thr Leu Pro Gly Ala
        435                 440                 445

Gly Ala Gly Ile Trp Tyr Phe Ile Thr Pro Lys Trp Glu Lys Leu Thr
    450                 455                 460

Asp Ala Thr Val Trp Lys Asp Ala Ala Thr Gln Ile Phe Phe Ser Leu
465                 470                 475                 480

Ser Ala Ala Trp Gly Gly Leu Ile Thr Leu Ser Ser Tyr Asn Lys Phe
                485                 490                 495

His Asn Asn Cys Tyr Arg Asp Thr Leu Ile Val Thr Cys Thr Asn Ser
            500                 505                 510

Ala Thr Ser Ile Phe Ala Gly Phe Val Ile Phe Ser Val Ile Gly Phe
        515                 520                 525

Met Ala Asn Glu Arg Lys Val Asn Ile Glu Asn Val Ala Asp Gln Gly
    530                 535                 540

Pro Gly Ile Ala Phe Val Val Tyr Pro Glu Ala Leu Thr Arg Leu Pro
545                 550                 555                 560

Leu Ser Pro Phe Trp Ala Ile Ile Phe Phe Leu Met Leu Leu Thr Leu
                565                 570                 575

Gly Leu Asp Thr Met Phe Ala Thr Ile Glu Thr Ile Val Thr Ser Ile
            580                 585                 590

Ser Asp Glu Phe Pro Lys Tyr Leu Arg Thr His Lys Pro Val Phe Thr
        595                 600                 605

Leu Gly Cys Cys Ile Cys Phe Phe Ile Met Gly Phe Pro Met Ile Thr
    610                 615                 620

Gln Gly Gly Ile Tyr Met Phe Gln Leu Val Asp Thr Tyr Ala Ala Ser
625                 630                 635                 640

Tyr Ala Leu Val Ile Ile Ala Ile Phe Glu Leu Val Gly Ile Ser Tyr
                645                 650                 655

Val Tyr Gly Leu Gln Arg Phe Cys Glu Asp Ile Glu Met Met Ile Gly
            660                 665                 670

Phe Gln Pro Asn Ile Phe Trp Lys Val Cys Trp Ala Phe Val Thr Pro
        675                 680                 685

Thr Ile Leu Thr Phe Ile Leu Cys Phe Ser Phe Tyr Gln Trp Glu Pro
    690                 695                 700

Met Thr Tyr Gly Ser Tyr Arg Tyr Pro Asn Trp Ser Met Val Leu Gly
705                 710                 715                 720

Trp Leu Met Leu Ala Cys Ser Val Ile Trp Ile Pro Ile Met Phe Val
                725                 730                 735

Ile Lys Met Tyr Leu Ala Pro Gly Arg Phe Ile Glu Arg Leu Lys Leu
            740                 745                 750

Val Cys Ser Pro Gln Pro Asp Trp Gly Pro Phe Leu Ala Gln His Arg
        755                 760                 765

Gly Glu Arg Tyr Lys Asn Met Ile Asp Pro Leu Gly Thr Ser Ser Leu
    770                 775                 780

Gly Leu Lys Leu Pro Val Lys Asp Leu Glu Leu Gly Thr Gln Cys
785                 790                 795
```

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:28:

```
GGRTCDATCA TRTTYTTRTA                                              20
```

(2) INFORMATION FOR SEQ ID NO:29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:29:

```
CCNAARGARA TGAAYAARCC NCC                                          23
```

(2) INFORMATION FOR SEQ ID NO:30:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:30:

```
GCNGTGAAGT ACACCACTTT NCC                                          23
```

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:31:

```
GGCYTCNGGG TAARCCACRA ANGC                                         24
```

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:32:

```
CGGTTCAATC TGTTGTCCGC ATCAGACATG                                   30
```

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:33:

```
GCAGGCTCGC GCGTCCGCTG                                              20
```

(2) INFORMATION FOR SEQ ID NO:34:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:34:

CCCGTATGTC GTACTCGTGA TCCTCCTCAT CCG                33

(2) INFORMATION FOR SEQ ID NO:35:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:35:

CCNCCRTGNG TDATCATNGG RAANCCC                      27

(2) INFORMATION FOR SEQ ID NO:36:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:36:

CCATCCACAC TACTGGAYYA RCAYTGNGTN CC                 32

(2) INFORMATION FOR SEQ ID NO:37:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:37:

CAGATTTCCT TCTCTTTATC TGCTGCATGG                    30

(2) INFORMATION FOR SEQ ID NO:38:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:38:

GGRTCDATCA TRTTYTTRTA NCKYTCNCC                     29

(2) INFORMATION FOR SEQ ID NO:39:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:39:

CCTGCACCAA CAGTGCCACA AGC                          23

(2) INFORMATION FOR SEQ ID NO:40:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (xi) SEQUENCE DESCRIPTION: SEQ ID NO:40:

CCAAGTACCT ACGCACACAC AAGCC                                      25

(2) INFORMATION FOR SEQ ID NO:41:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:41:

GGATTAATAC GGGACCATCC ACACTACT                                   28

In summary, the sequences of the Sequences Listing are as follows:

| SEQ ID | Type    | Sequence    | Corres Clone |
|--------|---------|-------------|--------------|
| 1      | N.A.    | nt 1–190    | phG2-3-a     |
| 2      | Protein | aa 1–63     |              |
| 3      | N.A.    | nt 1–190    | phG2-3-b     |
| 4      | Protein | aa 1–63     |              |
| 5      | N.A..   | nt 39–1254  | phG2-1       |
| 6      | Protein | aa 14–418   |              |
| 7      | N.A.    | nt 39–1635  | phG2-2       |
| 8      | Protein | aa 14–190   |              |
| 9      | Protein | aa 192–545  |              |
| 10     | N.A.    | nt 1317–1847| phG2-4-a     |
| 11     | Protein | aa 440–615  |              |
| 12     | N.A.    | nt 1317–1847| phG2-4-b     |
| 13     | Protein | aa 440–615  |              |
| 14     | N.A.    | nt 1540–2379| phG2-7-a     |
| 15     | Protein | aa 514–793  |              |
| 16     | N.A.    | nt 1540–2379| phG2-7-b     |
| 17     | Protein | aa 514–793  |              |
| 18     | N.A.    | nt 1–2397   |              |
| 19     | Protein | aa 1–797    |              |
| 20     | N.A.    | nt 1–2397   | pHGT2        |
| 21     | Protein | aa 1–797    |              |
| 22     | N.A.    | nt 1809–2397| phG2-8-a     |
| 23     | Protein | aa 604–797  |              |
| 24     | N.A.    | nt 1809–2397| phG2-8-b     |
| 25     | Protein | aa 604–797  |              |

The nucleic acid sequences described herein, and consequently the protein sequences derived therefrom, have been carefully sequenced. However, those of ordinary skill will recognize that nucleic acid sequencing technology can be susceptable to some error. Those of ordinary skill in the relevant arts are capable of validating or correcting these sequences based on the ample description herein of methods of isolating the nucleic acid sequences in question, and such modifications that are made readily available by the present disclosure are encompassed by the present invention. Furthermore, those sequences reported herein are within the invention whether or not later clarifying studies identify sequencing errors.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. An isolated nucleic acid encoding a glycine transporter comprising a sequence encoding the protein sequence of (i) SEQ ID 19 or (ii) a sequence corresponding to the protein sequence of SEQ ID 19 except that it has one or more of the following amino acid substitutions (1) $Ser^{102}$ to Gly, (2) $Ser^{124}$ to Phe, (3) $Ile^{279}$ to Asn, (4) $Arg^{393}$ to Gly, (5) $Lys^{457}$ to Asn, (6) $Asp^{463}$ to Asn, (7) $Cys^{610}$ to Tyr, (8) $Ile^{611}$ to Val, (9) $Phe^{733}$ to Ser or (10) $Ile^{735}$ to Val.

2. The nucleic acid of claim 1, comprising nucleotides 1-2391 of SEQ ID 18 or with a sequence that varies from nucleotides 1-2391 of SEQ ID 18 by having one or more of the following nucleotide substitutions (a) $T^6$ to C, (b) $A^{304}$ to G, (c) $C^{371}$ to T, (d) $C^{571}$ to T, (e) $T^{836}$ to A, (f) $A^{1116}$ to G, (g) $A^{1177}$ to G, (h) $G^{1371}$ to C, (i) $G^{1387}$ to A, (j) $G^{1829}$ A, (k) $A^{1831}$ to G, (l) $G^{2103}$ to A, (m) $T^{2198}$ to C, or (n) $A^{2203}$ to G.

3. A vector comprising the nucleic acid of claim 1 and an extrinsic promoter functionally associated therewith.

4. A transformed cell that expresses a recombinant glycine transporter, comprising a vector that comprises the nucleic acid of claim 1.

5. A method of producing a glycine transporter comprising growing the cells of claim 4 to produce the glycine transporter.

6. The method of claim 5 further comprising at least one of (a) isolating membranes from said cells, which membranes comprise the glycine transporter or (b) extracting a protein fraction from the cells which fraction comprises the glycine transporter.

* * * * *